US012350035B2

(12) United States Patent
Romrell et al.

(10) Patent No.: US 12,350,035 B2
(45) Date of Patent: Jul. 8, 2025

(54) ACCELEROMETER-BASED GAIT ANALYSIS

(71) Applicant: Fortify Technologies, LLC, Minneapolis, MN (US)

(72) Inventors: Gregory R. Romrell, Sandy, UT (US); Vanilyn Jereza Gomez, Cebu (PH); Mary Ann Antepuesto Lim, Cebu (PH)

(73) Assignee: Fortify Technologies, LLC, Minneapolis, MN (US)

( * ) Notice: Subject to any disclaimer, the term of this patent is extended or adjusted under 35 U.S.C. 154(b) by 802 days.

(21) Appl. No.: 16/921,270

(22) Filed: Jul. 6, 2020

(65) Prior Publication Data

US 2020/0330000 A1 Oct. 22, 2020

Related U.S. Application Data

(62) Division of application No. 15/434,502, filed on Feb. 16, 2017, now Pat. No. 10,716,495.

(Continued)

(51) Int. Cl.
*A61B 5/11* (2006.01)
*A61B 5/00* (2006.01)
*G06F 1/16* (2006.01)

(52) U.S. Cl.
CPC .............. *A61B 5/112* (2013.01); *A61B 5/002* (2013.01); *A61B 5/0022* (2013.01);
(Continued)

(58) Field of Classification Search
CPC ....... A61B 5/112; A61B 5/002; A61B 5/0022; A61B 5/6824; A61B 5/7278; A61B 5/742;
(Continued)

(56) References Cited

U.S. PATENT DOCUMENTS 8,784,274 B1 * 7/2014 Chuang ................. G06V 40/23
482/3
8,876,739 B2 11/2014 Salarian et al.
(Continued)

FOREIGN PATENT DOCUMENTS

WO 2013/046510 A1 4/2013

OTHER PUBLICATIONS

Requirement for Restriction/Election for U.S. Appl. No. 16/921,229, dated Apr. 20, 2023, (5 pages), United States Patent and Trademark Office, US.
(Continued)

*Primary Examiner* — Etsub D Berhanu
*Assistant Examiner* — Joseph A Tombers
(74) *Attorney, Agent, or Firm* — Alston & Bird LLP

(57) ABSTRACT

Embodiments of systems and methods determine one or more gait parameters using acceleration readings generated by an accelerometer coupled to a user. Gait parameters determined by various embodiments may include step length, step width, step time, single limb support time, or double limb support time. The accelerometer may be coupled to one of the user's arms. Exemplary systems may comprise an accelerometer, a processor, and a non-transitory computer readable medium (NTCRM). The processor may process acceleration readings from the accelerometer according to instructions stored on the NTCRM to determine the one or more gait parameters. The processor may communicate the one or more gait parameters to a receiving device. Some embodiments of the system may function as self-contained units and some embodiments may present information corresponding to gait parameters or recommendations regarding gait.

15 Claims, 14 Drawing Sheets

Related U.S. Application Data

(60) Provisional application No. 62/307,167, filed on Mar. 11, 2016.

(52) U.S. Cl.
CPC .......... *A61B 5/6824* (2013.01); *A61B 5/7278* (2013.01); *A61B 5/742* (2013.01); *G06F 1/163* (2013.01); *A61B 2562/0219* (2013.01)

(58) Field of Classification Search
CPC ............ A61B 2562/0219; A61B 5/681; A61B 5/7235; A61B 5/1122; G06F 1/163; G06F 2218/08; G06V 40/28; G06V 40/23; G06V 40/25; G01C 22/006; A63B 24/0062; A63B 2220/40; A63B 24/00; A63B 24/0003; A63B 2220/16; A63B 2220/22; A63B 2220/836; A63B 69/028; G01P 15/00
See application file for complete search history.

(56) References Cited

U.S. PATENT DOCUMENTS

| | | | |
|---|---|---|---|
| 8,961,439 B2 | 2/2015 | Yang et al. | |
| 9,445,720 B2 | 9/2016 | Janna et al. | |
| 9,782,122 B1 | 10/2017 | Pulliam et al. | |
| 2008/0045804 A1 | 2/2008 | Williams | |
| 2009/0079559 A1 | 3/2009 | Dishongh et al. | |
| 2012/0006112 A1* | 1/2012 | Lee ...................... | G01C 22/006 73/504.02 |
| 2012/0101411 A1 | 4/2012 | Hausdorff et al. | |
| 2013/0023798 A1 | 1/2013 | Greene et al. | |
| 2014/0066816 A1 | 3/2014 | McNames et al. | |
| 2014/0156215 A1 | 6/2014 | Eastman et al. | |
| 2014/0288681 A1* | 9/2014 | Watanabe ............ | A61B 5/1071 700/91 |
| 2014/0316305 A1 | 10/2014 | Venkatraman et al. | |
| 2014/0365169 A1* | 12/2014 | Pham .................. | G01C 22/006 702/160 |
| 2015/0230734 A1 | 8/2015 | Cheung | |
| 2016/0169703 A1 | 6/2016 | Omr et al. | |
| 2018/0020950 A1 | 1/2018 | Finch et al. | |
| 2018/0228683 A1* | 8/2018 | Zhang .................... | A61B 5/112 |
| 2019/0099134 A1 | 4/2019 | Bennett et al. | |

OTHER PUBLICATIONS

Requirement for Restriction/Election Mailed for U.S. Appl. No. 16/921,234, dated May 1, 2023, (6 pages), United States Patent and Trademark Office, US.
Requirement for Restriction/Election Mailed on May 12, 2023, for U.S. Appl. No. 16/921,249, 6 pages, United States Patent and Trademark Office, US.
U.S. Appl. No. 15/434,502, filed Feb. 16, 2017, U.S. Pat. No. 10,716,495, Issued.
U.S. Appl. No. 62/307,167, filed Mar. 11, 2016, Expired.
Del Din, Silvia et al. "Validation of an Accelerometer to Quantify a Comprehensive Battery of Gait Characteristics in Healthy Older Adults and Parkinson's Disease: Toward Clinical and at Home Use," IEEE Journal of Biomedical and Health Informatics. Apr. 2015, pp. 1-10. DOI: 10.1109/JBHI.2015.2419317.
Moe-Nilssen, Rolf et al. "Estimation of Gait Cycle Characteristics by Trunk Accelerometry," Journal of Biomechanics, vol. 37, (2004), pp. 121-126.
Sant' Ana, Anita et al., "Developing a Motion Language: Gait Analysis From Accelerometer Sensors," in 2009 3rd International Conference on Pervasive Computing Technologies for Healthcare, Apr. 1, 2009, pp. 1-8. IEEE.
Sant' Ana, Anita et al., "Gait Unsteadiness Analysis From Motion Primitives," Gerontechnology: International Journal on the Fundamental Aspects of Technology to Serve the Ageing Society, vol. 7, No. 2, (2008), (6 pages).
Satkunskeine, Danguole; Grigas, Vytautus; Eidukynas, V.; and Domeika, A. "Acceleration based evaluation of the human walking and running parameters." Journal of Vibroengineering, 11.3: pp. 506-510 (2009).
Sayeed, Taufique et al., "Comparison and Adaptation of Step Length and Gait Speed Estimators From Single Belt Worn Accelerometer Positioned on Lateral Side of the Body," 2013 IEEE 8th International Symposium on Intelligent Signal Processing (WISP), Sep. 16, 2013, (7 pages).
Tura, Andrea et al., "Gait Symmetry and Regularity in Transfemoral Amputees Assessed by Trunk Accelerations," Journal of Neuroengineering and Rehabilitation, (2010), 7:4. [Retrieved from the Internet Aug. 20, 2019] <URL: https://jneuroengrehab.biomedcentral.com/track/pdf/10.1186/1743-0003-7-4>.
United States Patent and Trademark Office, Final Office Action for U.S. Appl. No. 14/879,718, filed Jun. 14, 2019, (10 pages), USA.
United States Patent and Trademark Office, Final Office Action for U.S. Appl. No. 14/924,855, filed Feb. 21, 2018, (29 pages), USA.
United States Patent and Trademark Office, NonFinal Office Action for U.S. Appl. No. 14/879,718, filed Sep. 24, 2018, (24 pages), USA.
United States Patent and Trademark Office, NonFinal Office Action for U.S. Appl. No. 14/924,855, filed Oct. 5, 2017, (22 pages), USA.
Restriction Requirement for U.S. Appl. No. 16/921,261, dated May 26, 2023, (6 pages), United States Patent and Trademark Office, US.
NonFinal Office Action for U.S. Appl. No. 16/921,229, dated Jun. 23, 2023, (39 pages), United States Patent and Trademark Office, US.
NonFinal Office Action for U.S. Appl. No. 16/921,234, dated Jun. 14, 2023, (19 pages), United States Patent and Trademark Office, US.
NonFinal Office Action for U.S. Appl. No. 16/921,249, dated Jul. 5, 2023, (34 pages), United States Patent and Trademark Office, US.
NonFinal Office Action for U.S. Appl. No. 16/921,261, dated Jul. 3, 2023, (38 pages), United States Patent and Trademark Office, US.
Requirement for Restriction/Election for U.S. Appl. No. 16/921,277, dated Oct. 18, 2023, (6 pages), United States Patent and Trademark Office, US.
Final Rejection Mailed on Jan. 12, 2024 for U.S. Appl. No. 16/921,234, 19 page(s).
Non-Final Rejection Mailed on Jan. 26, 2024 for U.S. Appl. No. 16/921,277, 23 page(s).
Yang, Mingjing et al., "Assessing Accelerometer Based Gait Features to Support Gait Analysis for People with Complex Regional Pain Syndrome", 2010 Proceedings of the 3rd International Conference on Pervasive Technologies Relateed to Assistive Environments, (7 pages), https://doi.org/10.1145/1839294.
Advisory Action (PTOL-303) Mailed on Sep. 27, 2024 for U.S. Appl. No. 16/921,277, 3 page(s).
Final Rejection Mailed on Jul. 30, 2024 for U.S. Appl. No. 16/921,277, 22 page(s).
Non-Final Rejection Mailed on Aug. 1, 2024 for U.S. Appl. No. 16/921,234, 21 page(s).
Apple, "Apple Unveils Apple Watch—Apple's Most Personal Device Ever", published Sep. 9, 2014, [Retrieved on Feb. 4, 2025] Retrieved from the Internet: <https://www.apple.com/newsroom/2014/09/09Apple-Unveils-Apple-Watch-Apples-Most-Personal-Device-Ever/> (Year: 2014).
Apple, "Apple Watch Available in Nine Countries on Apr. 24", published Mar. 9, 2015 [Retrieved on Feb. 5, 2025], Retrieved from the Internet: <https://www.apple.com/newsroom/2015/03/09Apple-Watch-Available-in-Nine-Countries- on-April-24/> (Year: 2015).
Final Rejection Mailed on Feb. 11, 2025 for U.S. Appl. No. 16/921,234, 16 page(s).
Non-Final Rejection Mailed on Feb. 12, 2025 for U.S. Appl. No. 16/921,277, 32 page(s).
S. Chernbumroong et al., "Activity classification using a single wrist-worn accelerometer," 2011 5th International Conference on Software, Knowledge Information, Industrial Management and Applications (SKIMA) Proceedings, Benevento, Italy, 2011, pp. 1-6, doi: 10.1109/SKIMA.2011.6089975 (Year: 2011).

(56) References Cited

OTHER PUBLICATIONS

Advisory Action (PTOL-303) Mailed on Apr. 15, 2025 for U.S. Appl. No. 16/921,234, 3 page(s).

* cited by examiner

ACCELEROMETER-BASED GAIT ANALYSIS

CLAIM OF PRIORITY

This application is a divisional of U.S. patent application Ser. No. 15/434,502, filed Feb. 16, 2017, which claims the benefit of U.S. Provisional Application No. 62/307,167, filed Mar. 11, 2016, the entire contents of both of which are hereby incorporated by reference.

TECHNICAL FIELD

The systems and methods described herein relate to the use of accelerometers to estimate gait parameters.

BACKGROUND

Individuals propel themselves on foot in a variety of ways including walking, running, and ascending or descending stairs or sloped surfaces. Gait may be assessed in terms of a gait cycle, also called a stride. A stride begins when a reference foot (either the left or right) makes contact with the ground and ends when it next contacts the ground. A stride requires three instances when one of the feet makes contact with the ground—two contacts by the reference foot and one contact made by the opposite foot. During the stride, the reference foot spends some time in contact with the ground (called stance) and some time apart from the ground and moving forward (called swing). Both swing and stance of each foot are required to move forward.

A stride is composed of two steps. A step is the action occurring in the interval from the moment that one foot contacts the ground to the moment when the other foot contacts the ground. Step duration is not simply the stance time of one foot. During a walking stride, some time may be spent with both feet touching the ground (called double limb stance) and during a running stride, some time may be spent with neither foot on the ground. Thus, the stance times of each foot may add to more than duration of a walking stride and/or less than the duration of a running stride.

A step may be attributed to either the left foot or the right foot, though actions of both feet are necessary to take a step. A step is often attributed to the foot that is off the ground and moving forward during the step interval. However, steps taken on a gait mat or other instrument may be attributed to the foot touching the mat at the beginning of the step interval.

Steps have attributes sometimes referred to as gait parameters. Step duration is one such parameter and is defined by the beginning and end points of the step. Step frequency is the number of steps taken within a given time period and is the reciprocal of the average step duration during the time period. Step length is the component of the distance between the contact points defining the beginning and end of the step that is in the direction the individual is moving. The walking speed of an individual may be calculated by multiplying step length by step frequency. (Walking, as used herein, may refer to any step-taking activity including, but not limited to, walking, running, ascending, or descending.) Step width is the component of the distance between the contact points that is perpendicular to the direction the individual is moving in the plane of the ground. (Ground, as used herein, refers to any surface on which an individual takes steps and includes, without limitation, floors, stairs, pavement, and natural terrains.)

The portion of a step in which an individual supports his or her weight on a single leg may be referred to as single limb support (SLS) and the portion in which weight is supported on both limbs may be referred to as double limb support (DLS). During DLS, weight may not be supported equally by the legs and DLS may be distinguished from double limb stance which refers to the portion of the step during which both feet are touching the ground. In contrast, when only one foot is in contact with the ground, weight is presumed to be supported by the grounded foot, so there is no need to distinguish between single limb support from single leg stance. The proportions of each step spent in DLS and SLS may be indicative of gait health. In particular, longer periods of DLS may indicate difficulty taking steps. Some gait analysts classify every moment in the gait cycle as either SLS or DLS while others have a third category for transition between SLS and DLS. Under either classification system, both SLS and DLS may be indicative of general health and gait health in particular.

Gait analysis has been used not only to document gait abnormalities but also to determine the underlying causes of the abnormalities and, in some cases, to recommend a treatment. Gait analysis has traditionally been performed in a gait analysis laboratory. Instruments used to perform gait analysis detect a variety of measures associated with walking. Sensor mats, for example, are mats with numerous pressure sensors on which subjects may walk. Sensor mats, in combination with appropriate analytical tools, may generate measures such as those discussed above. However, laboratory-based gait-measuring equipment tends to be expensive, requires that subjects travel to the laboratory, and observes subjects for only the limited time that they are present at the laboratory. The benefits of gait analysis would be available to more patients if it could be conducted using less expensive equipment and the conclusions drawn from gait analysis would be more robust if clinicians could observe patients outside of the laboratory over longer time periods.

In recent years, accelerometers have become smaller, cheaper, more accurate, and more energy efficient. An accelerometer may refer to a device that measures either linear or angular acceleration. However, accelerometers measuring angular acceleration may also be called gyroscopes, gyrometers, or simply gyros. An accelerometer may also refer to a device that measures acceleration in more than one direction. Triaxial accelerometers have three axes that are at least approximately orthogonal to one another. The output readings from accelerometers may be plotted over time and can be viewed as a signal.

While coupling an accelerometer to a user's hip or leg may yield informative data regarding gait, many users prefer wearing accelerometers elsewhere. Wrist-worn accelerometers have become popular among consumers and may allow for observation of data among a greater number of users and for a greater proportion of the day than accelerometers worn on the hip or leg. However, wrist-worn accelerometers present challenges with respect to inferring gait parameters from the acceleration data.

SUMMARY

Embodiments of systems and methods determine one or more gait parameters using acceleration readings generated by an accelerometer coupled to a user. Gait parameters determined by various embodiments may include step length, step width, step time, single limb support time, or double limb support time. The accelerometer may be coupled to one of the user's arms. Exemplary systems may comprise an accelerometer, a processor, and a non-transitory computer readable medium (NTCRM). The processor may process acceleration readings from the accelerometer according to instructions stored on the NTCRM to determine the one or more gait parameters. The processor may communicate the one or more gait parameters to a receiving device. Some embodiments of the system may function as self-contained units and some embodiments may present information corresponding to gait parameters or recommendations regarding gait.

DETAILED DESCRIPTION

Figure 1:
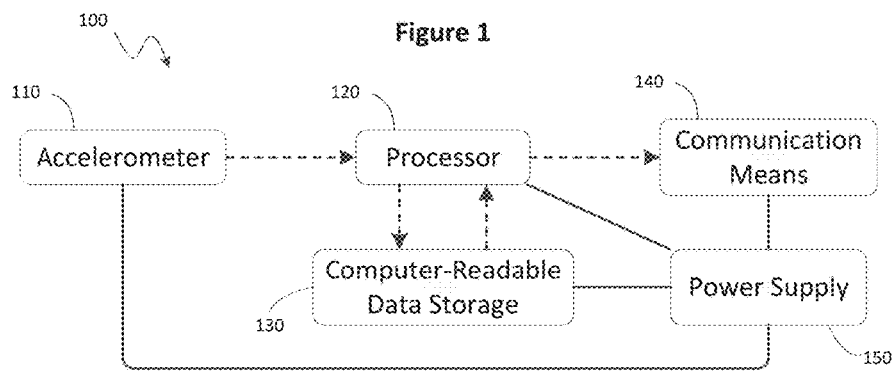
FIG. 1 presents a diagram illustrating an accelerometer-based system for estimating one or more gait parameters according to certain embodiments of the present disclosure.

Systems and methods estimate gait parameters using accelerometer readings. An accelerometer may be coupled to a user and at least some of the acceleration readings may correspond to the user's steps. An estimated gait parameter may be communicated through an output device, either to the user or to another individual.

Systems

A gait parameter is estimated by a system comprising an accelerometer. An accelerometer may refer to any device that measures either linear or angular acceleration, though accelerometers measuring angular acceleration may be referred to as gyroscopes, gyrometers, or gyros. An accelerometer may refer to a device that measures acceleration in more than one direction. For example, triaxial accelerometers measure acceleration on three axes that may be at least approximately orthogonal to one another. In addition to linear and angular acceleration, some accelerometers also contain a magnetometer that can orient accelerations relative to a magnetic field such as that of Earth. A so-called "9-axis accelerometer" contains a tri-axial accelerometer measuring linear acceleration along three orthogonal axes, angular acceleration around three orthogonal axes, and orientation relative to a magnetic field. A 9-axis accelerometer may also be referred to as an inertial measurement unit (IMU).

The accelerometer may be coupled to an individual whose steps are analyzed. In some embodiments, the accelerometer is coupled to an arm of the individual. In an exemplary embodiment, the accelerometer is coupled to the individual's wrist using a strap or similar means. In a second exemplary embodiment, the accelerometer may be coupled to the individual's torso by, for example, a belt around the hips or a lanyard around the neck.

In some embodiments, the accelerometer measures linear acceleration along three approximately orthogonal axes that are labeled x, y, and z. For triaxial accelerometers, unless otherwise indicated, the x axis runs approximately parallel to the user's dorso-ventral axis, which may also be approximately parallel to the direction the user walks; the y axis runs approximately parallel to the user's anterior-posterior axis, which may also run approximately parallel to the direction of gravity; and the z axis may run approximately parallel to the user's lateral axis. However, especially for wrist-worn accelerometers, users may swing their arms which can cause the x, y, and/or z axes of the accelerometer to lose alignment with the anatomical axes of the user as well as with the direction of gravity. As used herein, x, y, and z may refer to axes of a triaxial accelerometer, and may generally correspond to the dorso-ventral, anterior-posterior, and lateral axes of the user, respectively, accepting that the two sets of axes may not coincide. Likewise, the y axis my generally correspond to the direction of gravity with the understanding that the accelerometer axis may not align with the direction of gravity. Similarly, for biaxial accelerometers, unless otherwise indicated, the axes of the accelerometer may be referred to as the x axis and y axis, with the x axis generally corresponding to the user's dorso-ventral axis and the direction that the user is walking and the y axis generally corresponding to the user's anterior-posterior axis and to the direction of gravity, accepting that the accelerometer axes may not align with the anatomical, gravitational, or directional axes.

The accelerometer may be communicatively coupled to a processor. The processor may include one or more processing units (i.e. processors communicatively coupled to one another). The processor is communicatively coupled to and executes instructions stored on a computer readable data storage (CRDS) (also referred to herein as a non-transitory computer-readable medium). The instructions cause the processor to estimate a gait parameter. Embodiments of the CRDS may include random access memory (RAM) and various types of non-volatile memory including, but not limited to, read-only memory (ROM), programmable read-only memory (PROM), erasable programmable read-only memory (EPROM), and/or electrically erasable programmable read-only memory (EEPROM). Embodiments of the CRDS may include magnetic storage (such as hard drives, floppy disks, and magnetic tape) and/or optical storage (such as CDs and DVDs).

Time measuring means may be used to estimate some gait parameters. Time periods may be measured using a variety of means. Because processors typically perform calculations on a regular time cycle, some embodiments count processor cycles as a means for measuring time. If the accelerometer generates outputs at regular time intervals, embodiments may count the number of accelerometer outputs to measure the passage of time. Alternatively, a separate time-measuring device may be used to measure time periods. Examples of alternative time measuring devices include electric clocks such as quartz clocks, synchronous clocks, and radio-controlled clocks that are wirelessly synchronized with a time standard such as an atomic clock.

Embodiments of the system may also include a means for communicating a gait parameter. The communication means (also referred to as an "output device") may be, for example, a visual display, an audio speaker, or a tactile output to communicate the gait parameter to the user or another individual. Communication means may also include electromagnetic transmitters or physical connectors for communication of gait parameters to a second system or device. Some embodiments may communicate gait parameters and/or suggestions based on gait parameters to the user based on real-time analysis of the user's gait. For example, messages may suggest that a user take longer steps or that the user pause to balance on one foot.

System components named above may consume energy from a power source. Power sources may include various types of batteries as well as devices that collect ambient energy such as sunlight (e.g. photo-voltaic cells), body heat, and body motion. An exemplary embodiment powers its components with a lithium ion battery.

System embodiments may also include a user interface allowing a user to enter information into the computer. A user interface may include, for example, a key pad, touch screen, or microphone coupled to a voice recognition system. A user interface may be used, for example, for the user to enter information about walking conditions such as terrain or a recently sustained injury.

Components of the system may be communicatively coupled to other components. The processor, for instance, may receive information from the accelerometer, send information to the communication means (if any), and both send and receive information from the CRDS. Communicative coupling may be accomplished with or without physical connections such as wires. Any of the communications may be accomplished wirelessly using signal types including radio and infrared. Common wireless communication protocols include Bluetooth (IEEE 802.15), Wi-Fi (IEEE 802.11), cellular communication protocols, and infrared data association protocols. Embodiments using wireless communications may include components such as transmitters and receivers. Systems may also communicate with other devices or networks, for example a personal computer, smartphone or the Internet. In some embodiments, the user may receive and/or send information from the device through an Internet web site instead of or in addition to a user interface present in a device housing the accelerometer.

FIG. 1 illustrates a schematic diagram of a system (100) according to certain embodiments of the present disclosure. The system (100) includes an accelerometer (110) that sends outputs to a processor (120). The dashed line connecting the two components indicates that they are communicatively coupled; information may be transferred from one to another, but does not necessarily require a physical connection. The processor (120) executes instructions stored on a computer-readable data storage (CRDS) (130). The processor (120) may store and retrieve data, such as accelerometer data, from the CRDS (130) and process the data to determine a gait parameter. The processor (120) may communicate the gait parameter to a communication means (140). The components named above are powered by a power supply (150). While this diagram shows one power supply providing energy to each of the components, the system (100) may use multiple power sources. Any configuration of power sources may be used provided that each component receives power, either directly from a power supply or indirectly through other components.

Figure 2:
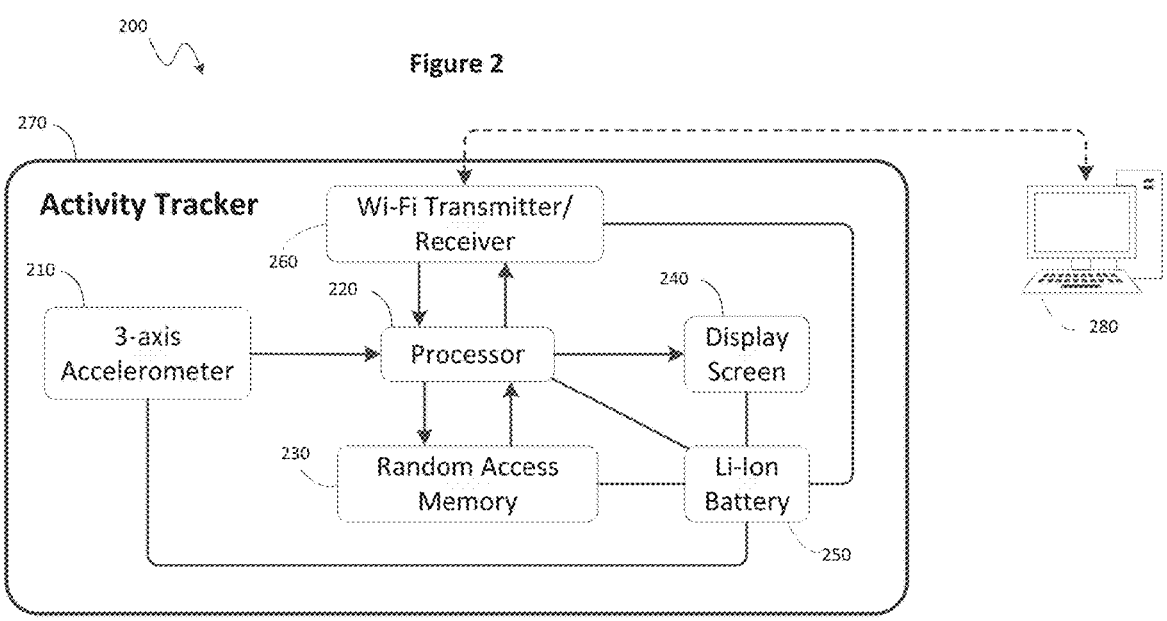
FIG. 2 presents a diagram illustrating an accelerometer-based system for estimating one or more gait parameters housed in a single device, according to certain embodiments of the present disclosure.

FIG. 2 illustrates a schematic diagram of a system (200) in a portable, self-contained activity tracker (270) according to certain embodiments of the present disclosure. The rectangle surrounding the components indicates that they are all housed in the same device. The activity tracker (270) includes a 3-axis accelerometer (210), a processor configured to function in the activity tracker (220), random access memory (RAM) (230), a display screen (240) visible from the outside of the device, and a rechargeable lithium-ion (Li-Ion) battery (250). The processor (220) executes instructions stored on the RAM (230). The display (240) may perform functions such as informing the user of gait parameters and/or goals based on gait parameters. From time to time, the activity tracker (270) may communicate with a second device (280) using radio signals. The activity tracker (270) contains a Wi-Fi transmitter-receiver (260) that exchanges data with the external device (280). The wireless communication may serve to communicate unprocessed or derived measures of physical activity to the external device (280) which may be communicatively coupled to networks such as the Internet. The wireless communication may be used to transfer updated instructions to the activity tracker (270) from the second device (280).

Figure 3:
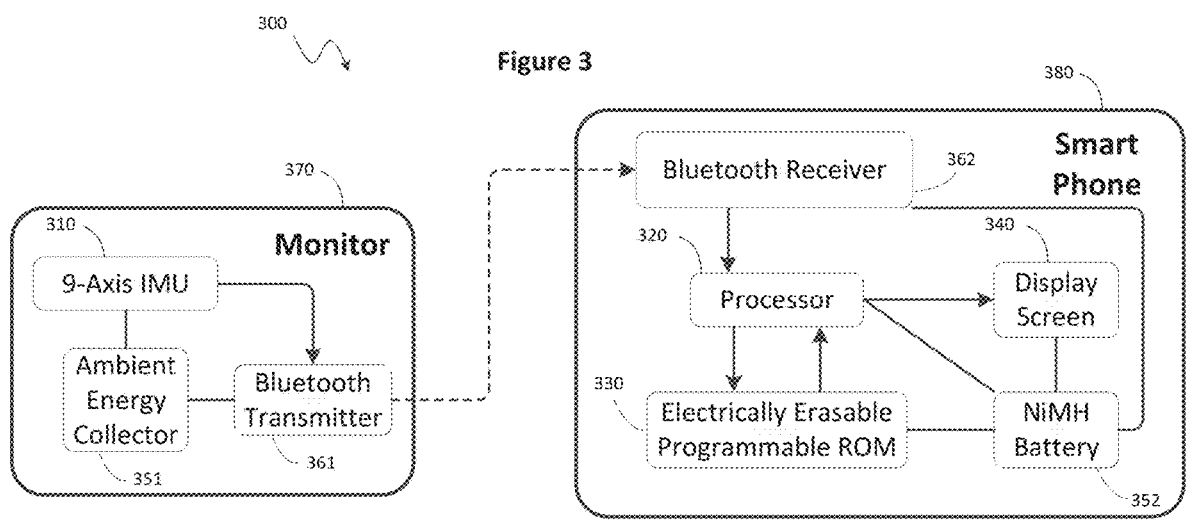
FIG. 3 presents a diagram illustrating an accelerometer-based system for estimating one or more gait parameters comprising a monitor device and separate smart phone according to certain embodiments of the present disclosure.

FIG. 3 illustrates a schematic diagram of a system (300) in which a motion monitor (370) wirelessly transfers acceleration data to an external device (380) for processing, according to certain embodiments. In this embodiment, the external device is a smartphone (380). The motion monitor (370) contains a 9-axis accelerometer/IMU (310), a Bluetooth transmitter (361), and an ambient energy collector (351) to power the other components. The ambient energy collector (351) may, for example, capture energy from the user's body heat. The Bluetooth transmitter (361) transmits raw (unprocessed) accelerometer data to a Bluetooth receiver (362) in the smartphone (380). The Bluetooth receiver (362) then relays the raw acceleration data to the processor (320) which, in turn, processes the acceleration data according to instructions stored on an electrically erasable programmable read-only memory (EEPROM) (330) and determines a gait parameter. The processor (320) may then communicate the gait parameter, or message based thereon, to a user via the display screen (340) on the smartphone (380). Components in the smartphone (380) are powered by a nickel metal-hydride (NiMH) battery (352). The smartphone (380) could, optionally, communicate raw or processed acceleration data to other external devices via cellular frequencies and data protocols. The smartphone could also, optionally, be used as an input device into which a user could enter data such as walking terrain, pain level, or health condition.

Figure 4:
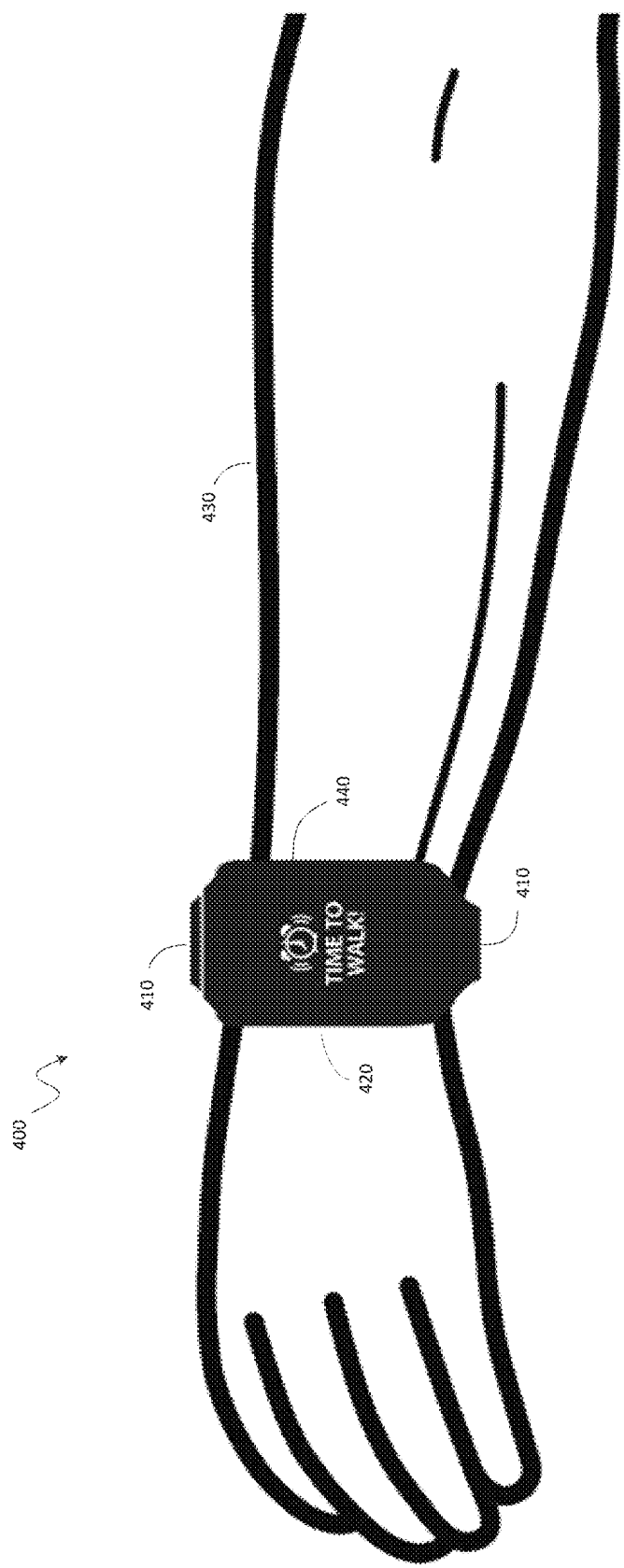
FIG. 4 illustrates an embodiment of a wrist-worn device according to certain embodiments of the present disclosure.

FIG. 4 illustrates an embodiment of a wrist-worn accelerometer device (400). Wrist straps (410) coupled to the device housing (420) keep the device housing (420) in an approximately fixed orientation relative to the forearm (430). The device housing (420) houses a triaxial accelerometer (not shown). Thus, as the angle of the forearm (430) changes relative to gravity, the gravitational pull along each of the axes may change. The device housing (420) comprises a display screen (440) that may display messages to the user. This particular embodiment (400) may remind the user to walk.

Methods—

System embodiments may determine one or more gait parameters using a variety of methods. Some method embodiments estimate gait parameters using accelerometer data from an accelerometer coupled to a user's wrist or another part of the user's arm. An arm may approximate a line segment swinging on the pivot point of the shoulder. Typically, individuals under ordinary conditions swing one of their arms once per stride. That is, the arm returns to its starting position and direction once every two steps. The amount of forward arm swing, as measured by either angle or arc length, may be different than the amount of backward arm swing.

During a cycle of an arm swing, combined linear acceleration may reach a minimum at both the end of a forward arm swing and at the end of a backward arm swing, in each case when the angle of the arm relative is momentarily fixed. Conversely, the maximum combined accelerations during a stride may occur when the arm is mid-swing and approximately parallel to the force of gravity. There are often two peaks per stride—one during the forward arm swing and one during the backward arm swing. The moment at which a foot makes contact with the ground corresponds approximately to a minimum acceleration of an arm. The foot that is on the same side as a wrist-worn accelerometer makes contact at approximately the end of the backward arm swing and the foot opposite the side of the accelerometer makes contact at approximately the end of the forward arm swing.

Figure 5:
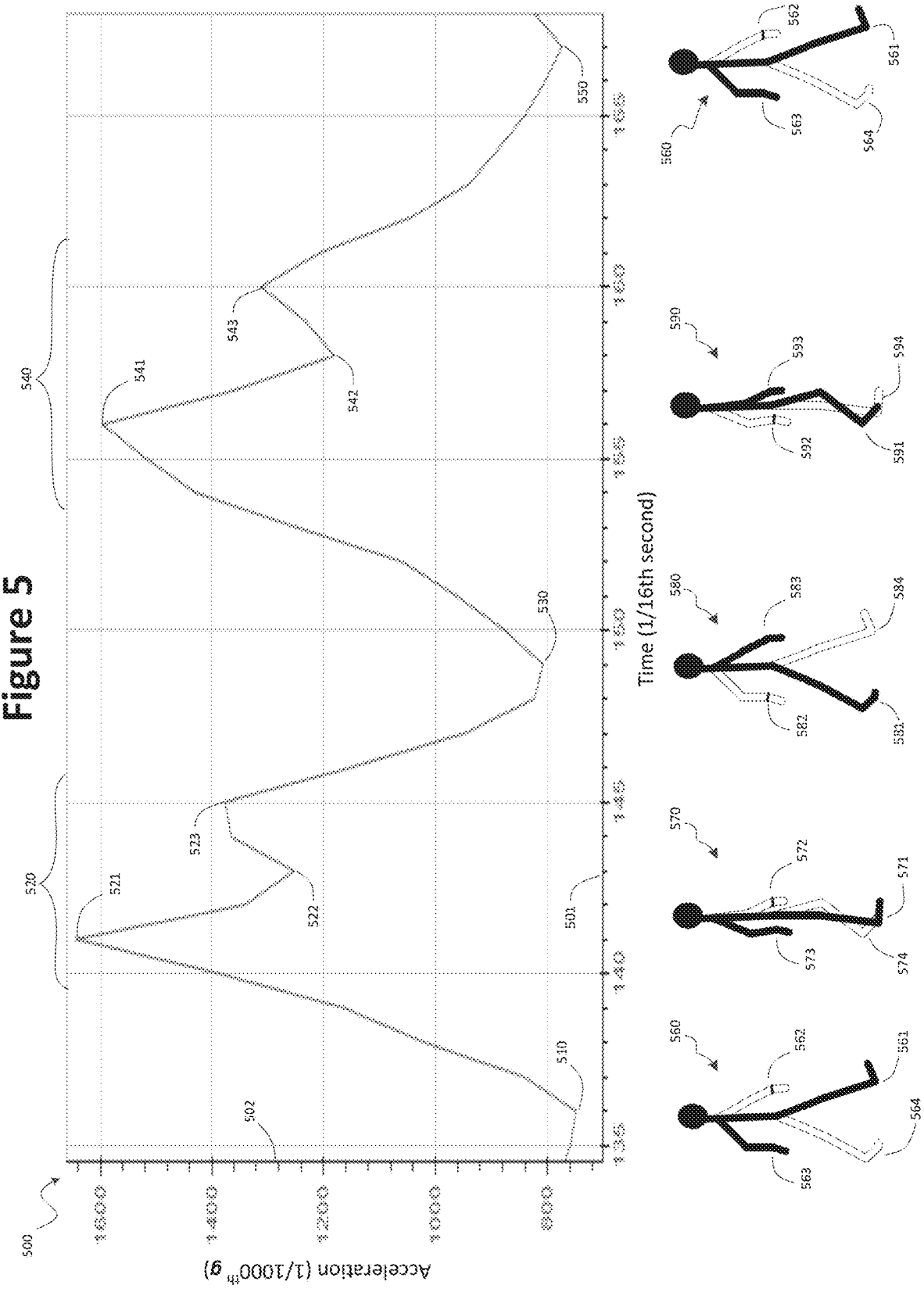
FIG. 5 presents a plot of the magnitude of acceleration of a wrist-worn accelerometer during two steps and presents figures illustrating limb positions corresponding to the acceleration readings.

FIG. 5 presents a sample of acceleration data (500) from a user's wrist-worn accelerometer while taking two steps. The stick figures (560, 570, 580, 590) illustrate the position of the user's limbs corresponding to peaks and valleys in the data. The x axis (501) represents time in 1/16th second increments and the y axis (502) corresponds to the combined magnitude of acceleration in 1/1000 of g. increments along the axes of a triaxial accelerometer. Each of the two steps comprises a peak (520, 540) which are separated from adjacent peaks by three valleys (510, 530, 550). The peak for each of the steps (520, 540) is bifurcated into two sub-peaks (521, 523; 541, 543). Within each peak, the two sub-peaks are separated from one another by a trough (522, 542). The cause of these bifurcations is unknown, but they appear typical of most walking data from wrist-worn accelerometers.

In FIG. 5, each of the stick figures (560, 570, 580, 590) illustrate the position of the limbs corresponding to the acceleration reading of the peak or valley above the particular stick figure. The first step begins when the user's right heel (561) first contacts the ground. At this moment, the arm with the accelerometer (the left arm, 562) is momentarily motionless as the direction of arm swing changes and the combined acceleration at the wrist is approximately that of gravity (g). This corresponds to the valley (510) that is approximately at g (800/1000 g). The right arm (563) is in the back-most position of its swing and the left leg (564) is pushing off of the left foot. Peak (520) occurs when the arm with the accelerometer (the left arm, 572) is mid-swing and pointing approximately parallel to the force of gravity as it swings backward. The right arm (573) is also mid-swing and approximately parallel to gravitational force. Weight is supported on the right leg (571) as the left leg (574) is swinging. The first step ends and the second step begins when the left heel (584) contacts the ground. The left arm (with accelerometer, 582) is motionless at the back-most portion of its swing and the accelerometer registers only the force of gravity corresponding to valley (530). The right arm (583) is at the forward-most part of its swing and the right leg (581) is pushing off the ground. Peak (540) occurs when the arm with the accelerometer (the left arm, 592) is mid-swing and pointing approximately parallel to the force of gravity as it swings forward. The right arm (593) is also mid-swing and approximately parallel to gravitational force. Weight is supported on the left leg (591) as the right leg (594) is swinging. The second step ends when the left heel (564) contacts the ground as it did for the first step.

Gait Speed

The rate at which an individual moves on foot, gait speed, may be computed as the ratio of step length to step duration—the amount of time from the beginning of a step to the end of the step. Embodiments estimating gait speed estimate both step length and step duration.

Step Duration

A step begins at the moment that one of the feet first makes contact with the ground and ends at the moment the other foot next contacts the ground. Since foot contact occurs at approximately the moment that the arms have reached the end of their respective swings, combined acceleration along the x and y axes of an accelerometer reaches a minimum at the time one step ends and the next begins. Step duration (SD) may therefore be estimated as the time between two step minima—those acceleration minima corresponding to the end point of an arm swing as opposed the trough between the sub-peaks or other local minima caused by noise in the data. A minimum may refer to an accelerometer reading that is flanked on both sides by higher readings; the reading immediately preceding a minimum and the reading immediately following a reading are each greater than the minimum data point.

Figure 6:
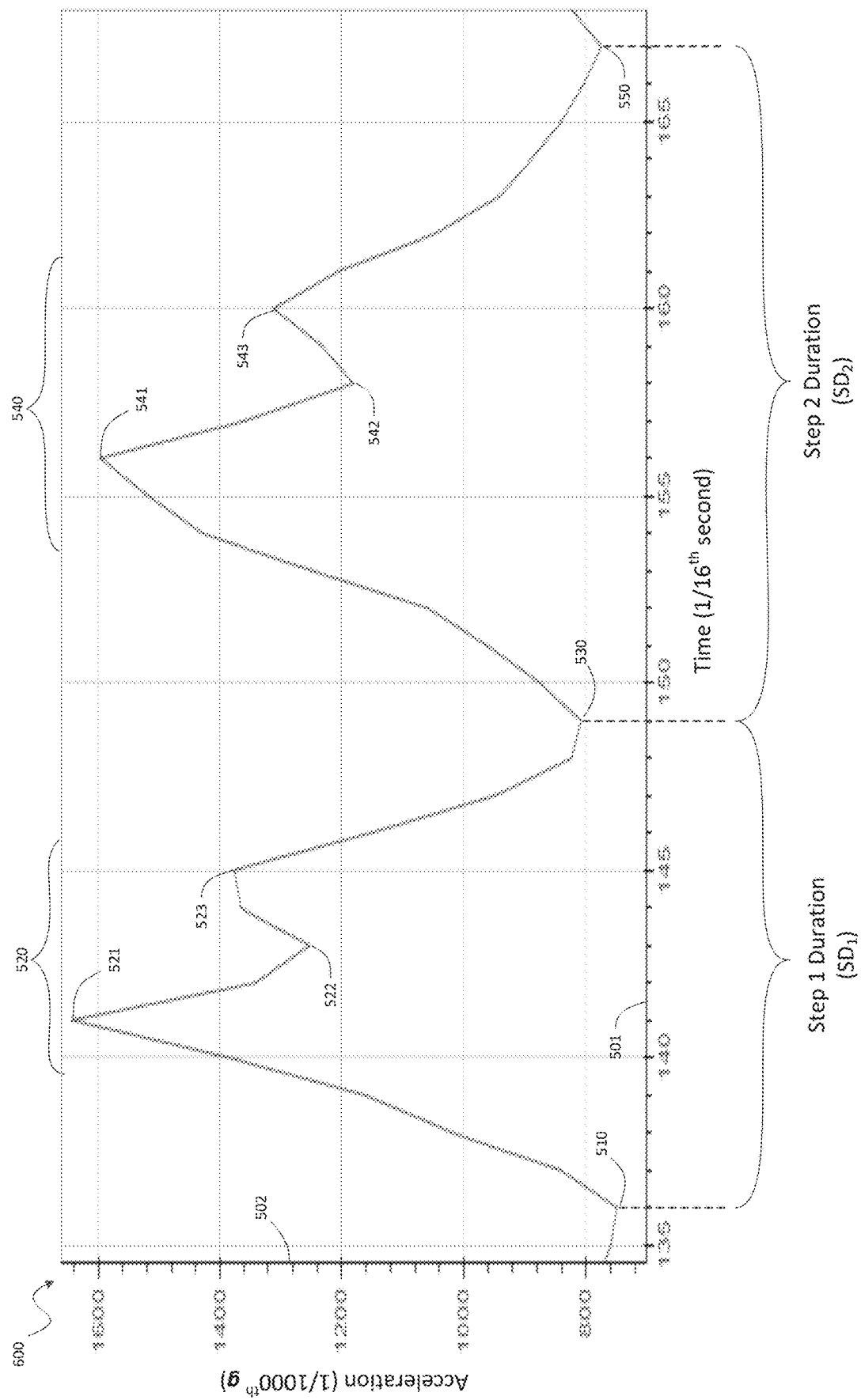
FIG. 6 presents a plot of acceleration of a wrist-worn accelerometer during two steps and illustrates the duration of each step as estimated by features of the accelerometer data, according to certain embodiments of the present disclosure.

FIG. 6 presents the acceleration plot of FIG. 5 with duration of the first and second steps (SD1 and SD2, respectively) indicated by brackets. Step duration may be estimated as the difference between the time at which one step minimum occurred and the time at which the next step minimum occurred. In FIG. 6, the first step begins at the minimum (510) occurring at approximately 136 16ths of a second and ends at the minimum (530) occurring at approximately 149 16ths of a second. Thus, SD1=(149−136)/16 of a second or 13/16ths of a second. Step 2 begins at 149 16ths of a second and ends at the minimum (550) occurring at approximately 167 16ths of a second. SD2=(167−149)/16 of a second or 19/16ths of a second.

To determine the duration of a particular step via processor implemented instructions, some embodiments analyze accelerometer data as a "sliding window." A data window (window) refers to a group of accelerometer readings (also called data points) generated at a given amount of time relative to a reference data point. The readings in a window are considered in an analysis. For example, some embodiments analyze data generated in the half second before the reference data point. If analysis takes place in real time, the reference data point may be the most recently generated data point. But post-hoc analysis may use a past reference data point that progresses to another reference data point (also referred to as a focal data point) once the window associated with the first data point has been analyzed. The window "slides" in that the reference data point advances by one reading (or a number of readings less than the number of readings in the window) for each analysis. Thus, for sliding windows advancing by a single data point from one analysis to the next, the group of readings being analyzed differs by only the first and last data points in the window; the first data point is new and the last data point is no longer part of the group considered. Some windows may slide by advancing more than one data point at a time provided there is at least one common data point between two windows. Some embodiments use contiguous windows (in which the first data point in a window is the reading immediately following the last data point of the previous window) and some embodiments use separated windows (in which windows are separated by unanalyzed data points.

Some embodiments adjust window size as a function of acceleration data. For example, some embodiments analyze a window that is approximately half the duration of the fundamental frequency determined by an autocorrelation function. (Note that the autocorrelation function may yield the typical step duration over a period of time but does not determine the duration of a particular step.) If halving the duration yields a fractional number of data points, some embodiments may, for example, round down to the time period with the next lowest whole number of data points.

Some embodiments use sliding windows as a tool to distinguish step minima (those marking the farthest point of an arm swing) from other local minima. A local minimum may refer to a downward inflection point—an acceleration reading flanked on both sides by higher readings. For example, some embodiments count a point as a step minimum only if is the lowest reading in the window that is flanked by higher points. For these embodiments, determining an appropriate window size is important to identify steps. If a window is too long, steps may be missed and if the window is too short, local minima that are not steps may be counted as such. After identifying the step minima in the acceleration signal, the time between each identified step minimum may approximate the time for an individual step.

Figure 7:
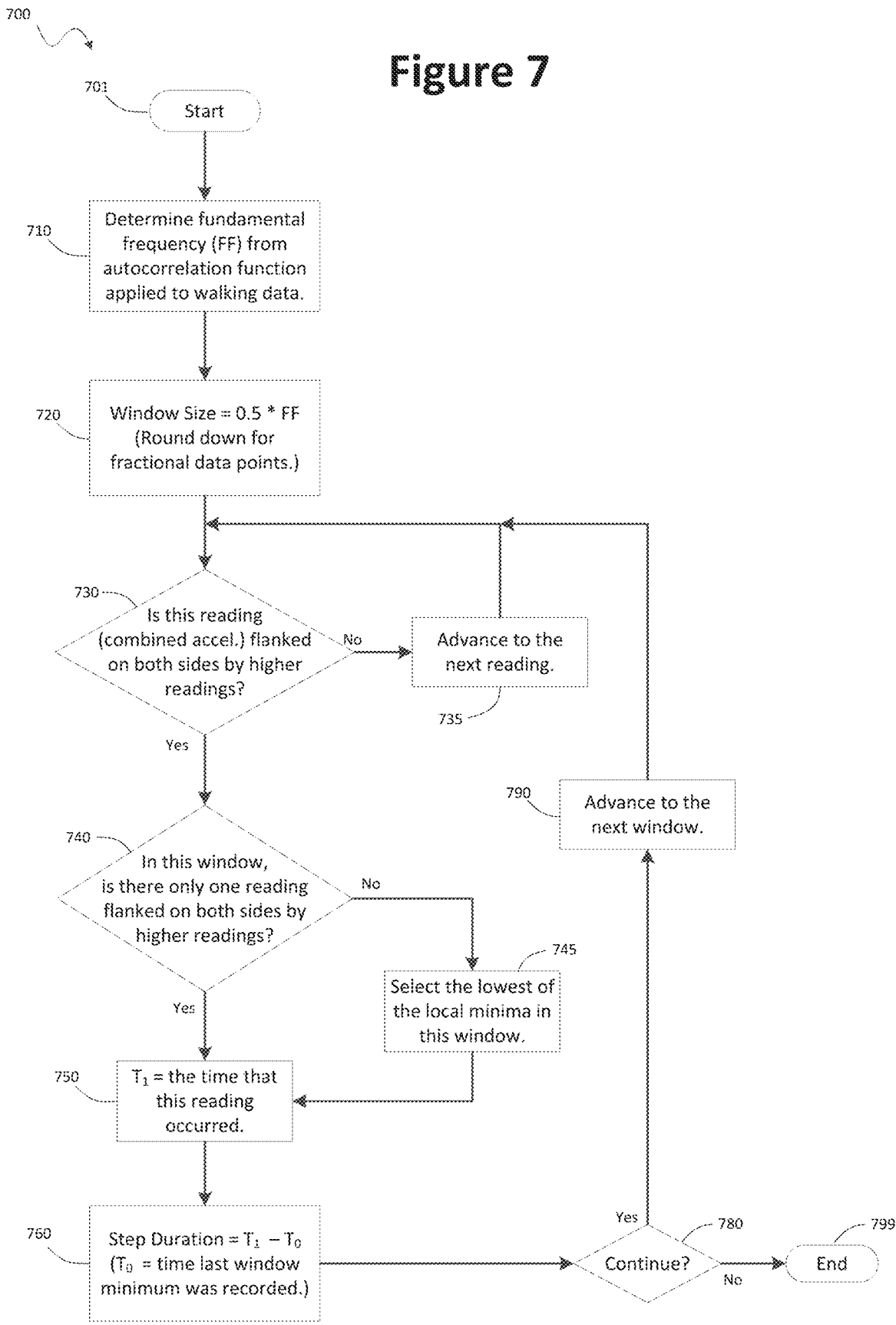
FIG. 7 presents a flow chart illustrating an accelerometer-based method for estimating step duration, according to certain embodiments of the present disclosure.

FIG. 7 presents a flow chart illustrating a computer-implemented method (700) of determining step duration, according to certain embodiments. After the start (701), the fundamental frequency from an autocorrelation function is determined (710). Window size is set at half the fundamental frequency of the autocorrelation (720). If half the time of the fundamental frequency includes a fraction of an accelerometer reading, the window size rounds down to the next whole number of readings (720). Starting with the first reading in a window, the method (700) queries whether the reading is lower than both the immediately previous reading and the immediately following reading (730). If not, analysis proceeds to the next reading (735). If the reading is a local minimum (flanked by greater readings), the method then queries whether the reading is the only local minimum in its window (740). If so, the single local minimum is selected. If there are one or more other local minima in the window, the lowest of the local minima is selected (745). The time of the selected local minimum ($T_i$) is then accessed (750). Step duration is estimated as the time between $T_1$ and $T_0$—the time at which the previous step minimum occurred (760). The method (700) then queries whether to continue (780). If so, analysis proceeds to the next window (790). If not, the method (700) ends (799).

Step Length

Determining step length from wrist-worn accelerometer data has proven challenging, particularly when data on angular acceleration is absent. Some embodiments calculate step length as a function of the distance the hand travels when swinging during a step.

Figure 8:
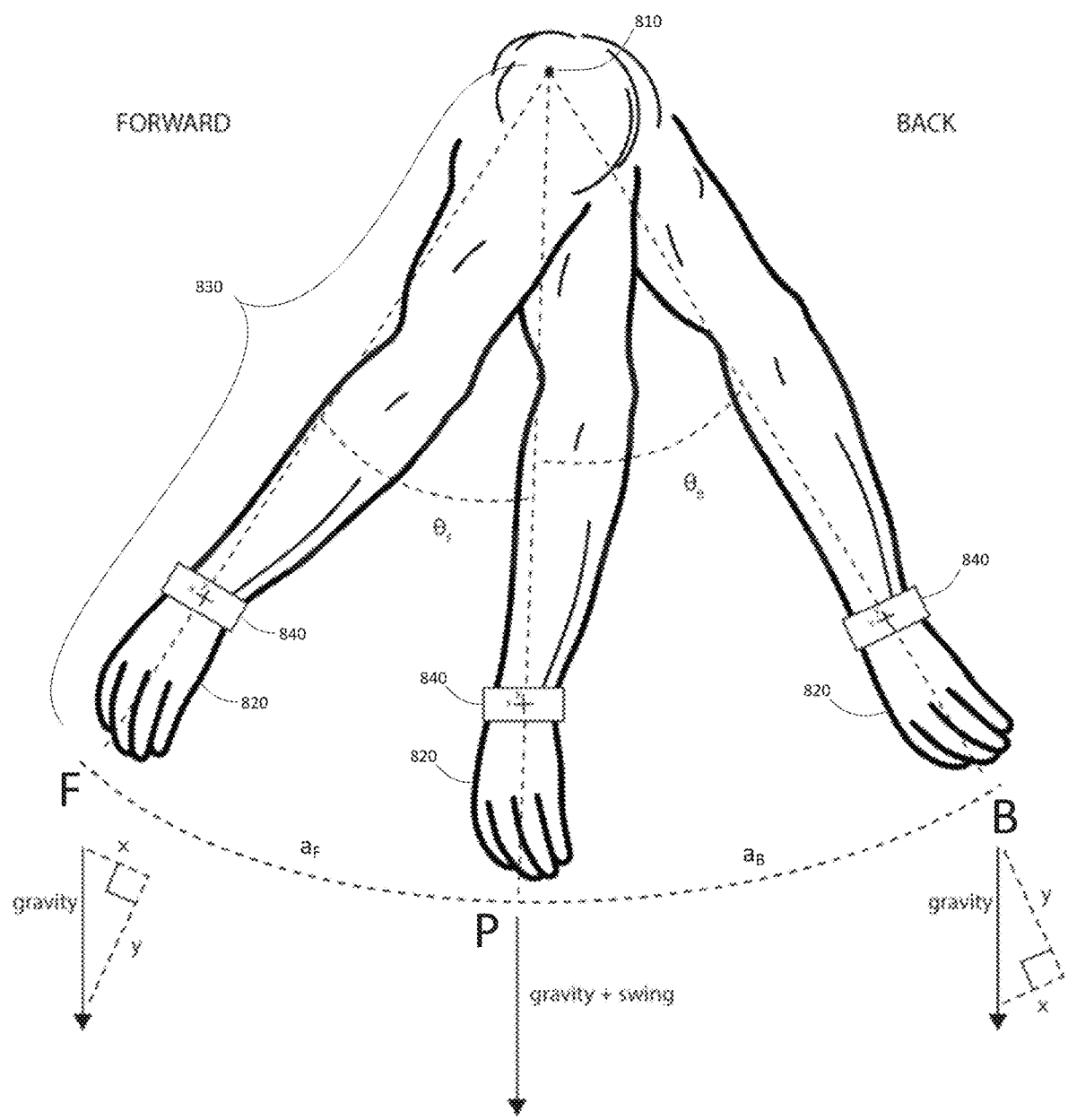
FIG. 8 presents a schematic diagram illustrating the changing orientation of an accelerometer on a swinging arm, relative to gravity.

FIG. 8 illustrates arm position as a simple line segment pivoting around a point. The shoulder (810) is the pivot point and the hand (820) functions as the end of the line segment. The arm from shoulder to hand is represented as a dashed line segment (830) having a length of L. An accelerometer (840) having two orthogonal axes (x and y) is coupled to the wrist. In position P, the arm is parallel to the direction of gravity. Position F is the forward-most position of the arm during a swing and position B is the back-most position of the arm. The angle of arm swing between position P and position F is labeled $\theta_F$ and the angle of arm swing between position P and position B is labeled $\theta_B$. The arc length, the distance the hand travels from position P to position F, may be referred to as $a_F$ and the arc length the hand travels from position P to position B, may be referred to as $a_B$. $a_F$ may be calculated as $\theta_F * L$ and as may be calculated as $\theta_B * L$ where $\theta_F$ and $\theta_B$ are measured in radians.

As FIG. 8 illustrates, the force of gravity acts like a constant acceleration in the direction opposite gravitational pull. In position P, downward force is caused both by gravity and the centripetal force of the arm swinging on its axis. In positions F and B, when the arm is momentarily stationary, gravity is the primary force acting on the accelerometer. Some embodiments determine values for $\theta_F$ and $\theta_B$ by measuring the components of gravitational pull on the x and y axes of an accelerometer at positions F and B, respectively. For example, some embodiments measuring acceleration along x and y axes may calculate either $\theta_F$ or $\theta_B$ as the arctangent of the ratio of force along the x axis to force along the y axis or as the arccosine of the ratio of acceleration along the y axis to total gravitational pull. If step length is calculated as a function of total arm swing (the sum of $a_F$ and $a_B$), the method need not distinguish whether the arm swing is in the forward ($a_F$) or backward ($a_B$) direction. Some embodiments measuring acceleration along three axes determine $\theta$ as a function of how gravitational pull is distributed among the three axes and may compensate for the accelerometer rotating about the wrist as the arm swings.

The arc length that the hand travels during an arm swing is a function of the sum of $a_F$ and $a_B$ ($a_{total}$) and the length of the user's arm (L). Some embodiments use a standard length for L. The standard may be a global measure of central tendency for arm length or may be informed by factors such as the user's height, age, gender, or an actual measurement of the user's arm. As explained for FIG. 8, total arc length ($a_{total}$) may be calculated, for example, as $\theta_{total} * L$ where $\theta_{total}$ is measured in radians. Some embodiments calculate step length as equal to the arc length of arm swing. Some embodiments calculate step length as a function of the arc length of arm swing. For example, some embodiments may multiply the arc length of arm swing by a coefficient to obtain step length.

Figure 9:
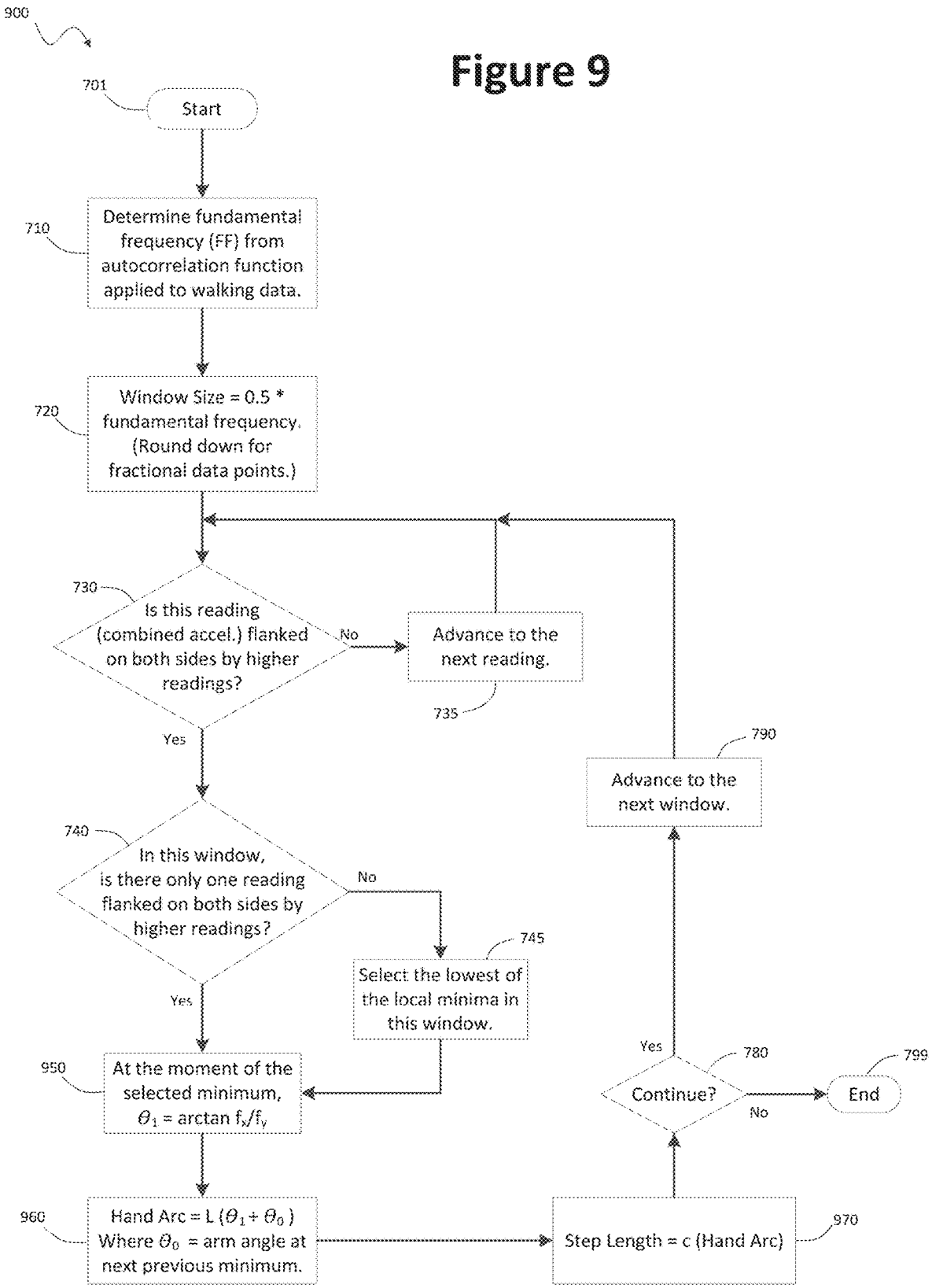
FIG. 9 presents a flow chart illustrating an accelerometer-based method for estimating step length, according to certain embodiments of the present disclosure.

FIG. 9 is a flow chart illustrating a method (900) for estimating step length, according to certain embodiments. After the start (701), the fundamental frequency (FF) for a sample of data using an autocorrelation function is determined (710). Window size is set at half the fundamental frequency of the autocorrelation (720). If half the time of the fundamental frequency includes a fraction of an accelerometer reading, the window size rounds down to the next whole number of readings (720). Starting with the first reading in a window, the method (900) queries whether the reading is lower than both the immediately previous reading and the immediately following reading (730). If not, analysis proceeds to the next reading (735). If the reading is a local minimum (flanked by greater readings), the method then queries whether the reading is the only local minimum in its window (740). If so, the single local minimum is selected. If there are one or more other local minima in the window, the lowest of the local minima is selected (745). Once a minimum is selected, arm angle $\theta_1$ (the method does not distinguish whether the arm swing is in the forward or backward direction) may be calculated as arctangent of the ratio of measured acceleration along the accelerometer's x axis ($f_x$) to measured acceleration along the accelerometer's y axis ($f_y$) (950). Next, hand arc length is calculated by multiplying the sum of $\theta_1$ and $\theta_0$ (each expressed in radians) by the length of the user's arm (L) (960). $\theta_0$ is the arm angle calculated for the immediately previous combined acceleration minimum. Step length is estimated as the hand arc length of the arm swing multiplied by a constant c (970). The method (900) then queries whether to continue (780). If so, analysis proceeds to the next window (790). If not, the method (900) ends (799).

Single and Double Limb Support

Single limb support (SLS) and double limb support (DLS) may be important measures for assessing gait health. Those with balance disorders or other difficulties walking tend to exhibit a higher proportion of their gait cycle in DLS and a lower proportion in SLS. Some embodiments estimate SLS and/or DLS through processor-implemented analysis of an acceleration signal wherein the accelerometer is attached to the arm of a user. In some embodiments, the accelerometer may be a triaxial accelerometer and the processor analyses the combined magnitude of acceleration from all three axes.

Figure 10:
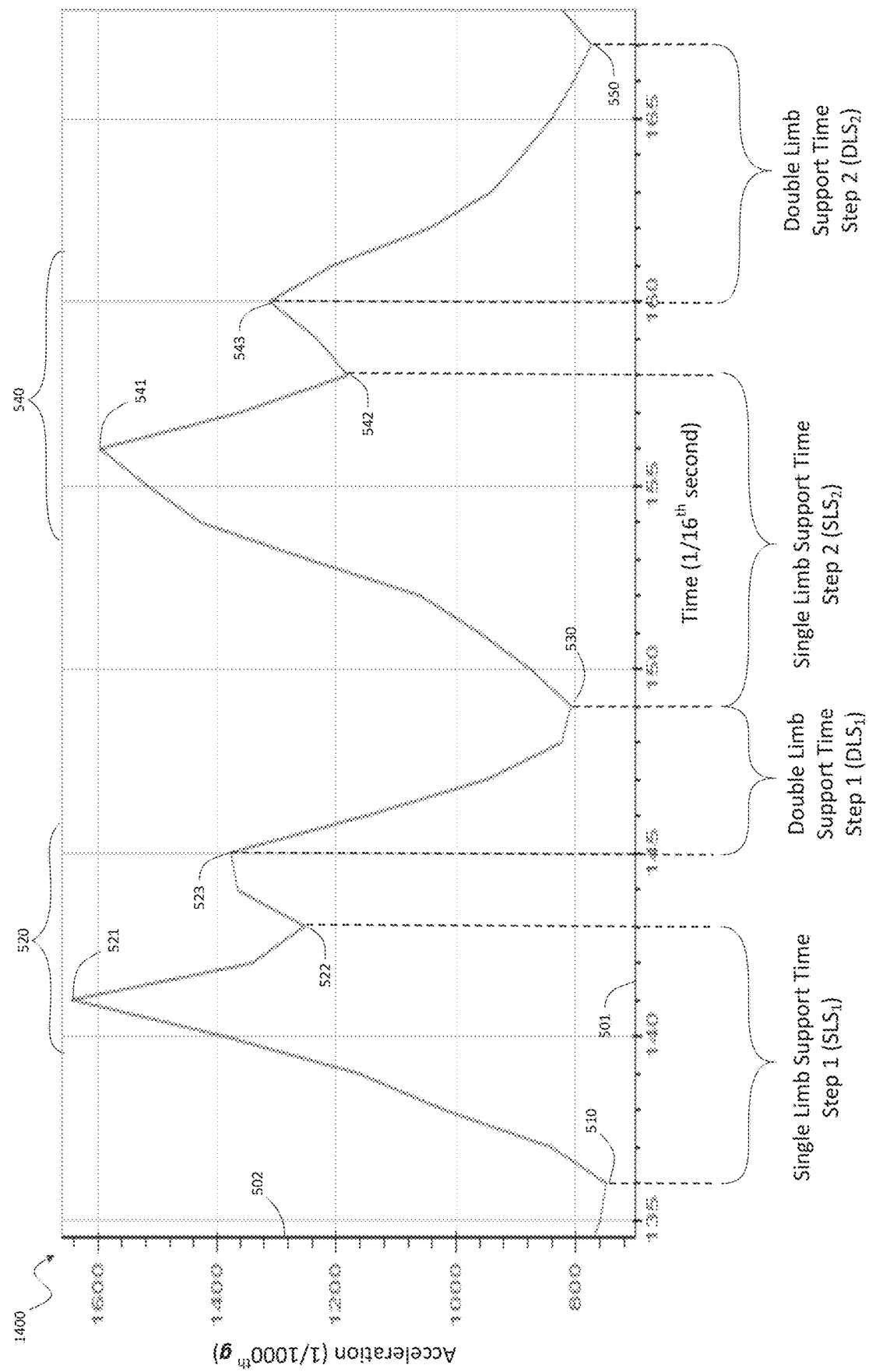
FIG. 10 presents a plot of acceleration of a wrist-worn accelerometer during two steps and illustrates a portion of each step attributed to SLS and to DLS according to certain embodiments of the present disclosure.

FIG. 10 presents the acceleration plot of FIG. 5 and delineates time periods corresponding to durations of both SLS and DLS, according to certain embodiments. The specified time periods may not correspond exactly to the times when SLS and/or DLS is occurring but estimate the amount of time spent in each state. In this embodiment, the times for SLS and DLS do not add to the total step duration (SD). Time in a step not spent in SLS or DLS may be referred to as the transitional phase of a step. For each of the two steps, the embodiment estimates the duration of SLS as the time from the step minimum marking the beginning of the step (510, 530) to the local minimum separating the two sub-peaks of the step (522, 542, respectively). SLS time for the first step (SLS1) is estimated as being the amount of time from step minimum 510 to local minimum 522 which is approximately 7/16ths of a second. The proportion of the first step spent in SLS is estimated to be SLS1/SD1 or 8/13ths of the step. Likewise, SLS time for the second step (SLS2) is estimated as the amount of time from step minimum 530 to local minimum 542 which is approximately 9/16ths of a second. The proportion of the second step spent in SLS is estimated to be SLS2/SD2, or 9/18ths (half) of the step. For each of the two steps shown in the plot, the duration of DLS is estimated to be the time from the second sub-peak of the step (523, 543) to the step minimum marking the end of the step during which the sub-peaks occurred (530, 550, respectively). DLS time for the first step (DLS1) is estimated as being the amount of time from sub-peak 523 to step minimum 530 which is approximately 4/16ths (one quarter) of a second. The proportion of the first step spent in DLS is estimated to be DLS1/SD1 or 4/13ths of the step. Likewise, DLS time for the second step (DLS2) is estimated as the amount of time from sub-peak 543 to step minimum 550 which is approximately 7/16ths of a second. The proportion of the second step spent in DLS is estimated to be DLS2/SD2, or 7/18ths of the step.

Similar to embodiments described for estimating step duration, some processor-implemented embodiments determine a time duration for a first sliding window. Some embodiments use a predetermined time span for the sliding window. For example, some embodiments analyze data generated in the third (⅓) of a second before the reference data point while some analyze data generated in the half (0.5) of a second before the reference data point. However, some embodiments adjust the window size as a function of acceleration data. For example, some embodiments analyze data points in a window that is approximately half the fundamental frequency determined by an autocorrelation function applied to accelerometer walking data. If halving the fundamental frequency yields a fractional number of data points, some embodiments may, for example, round up or down to the time period with the next highest or lowest, respectively, whole number of data points.

Some embodiments use sliding windows to identify beginning and end points of steps. A step may occur between two step minima where a step minimum may refer to an acceleration minimum that takes place when the arm has reached the end of its swing, either in the forward or backward positions. Some embodiments count a point as a step minimum only if is the lowest local minimum (a reading flanked on both sides by greater readings) in the window.

Some embodiments may determine a second sliding window that is shorter than the first sliding window. The second sliding window may serve to identify the trough separating the sub-peaks in a peak. As with the first sliding window, the second sliding window may, for example, be a fixed duration or may be a function of accelerometer readings. An embodiment may, for example, use a fixed duration of a quarter of a second. Alternatively, an embodiment may set the second sliding window as, for example, a quarter of the fundamental frequency determined by an autocorrelation function. Peaks and troughs, as defined by the second sliding window, are the highest local maximum (flanked on both sides by lower points) and the lowest local minimum (flanked on both sides by higher points) within a window.

Some embodiments calculate SLS time as the amount of time from a valley as determined according to the first sliding window to the next trough as determined by the second, shorter, sliding window. Within an episode of walking (a walk), the average SLS time per step may be calculated as the cumulative SLS time for a number of steps divided by the cumulative step duration for those steps. Some embodiments screen the data by discarding estimates for steps in which there are not at least two peaks and three valleys between two adjacent valleys as determined by the first (longer) sliding window.

Figure 11:
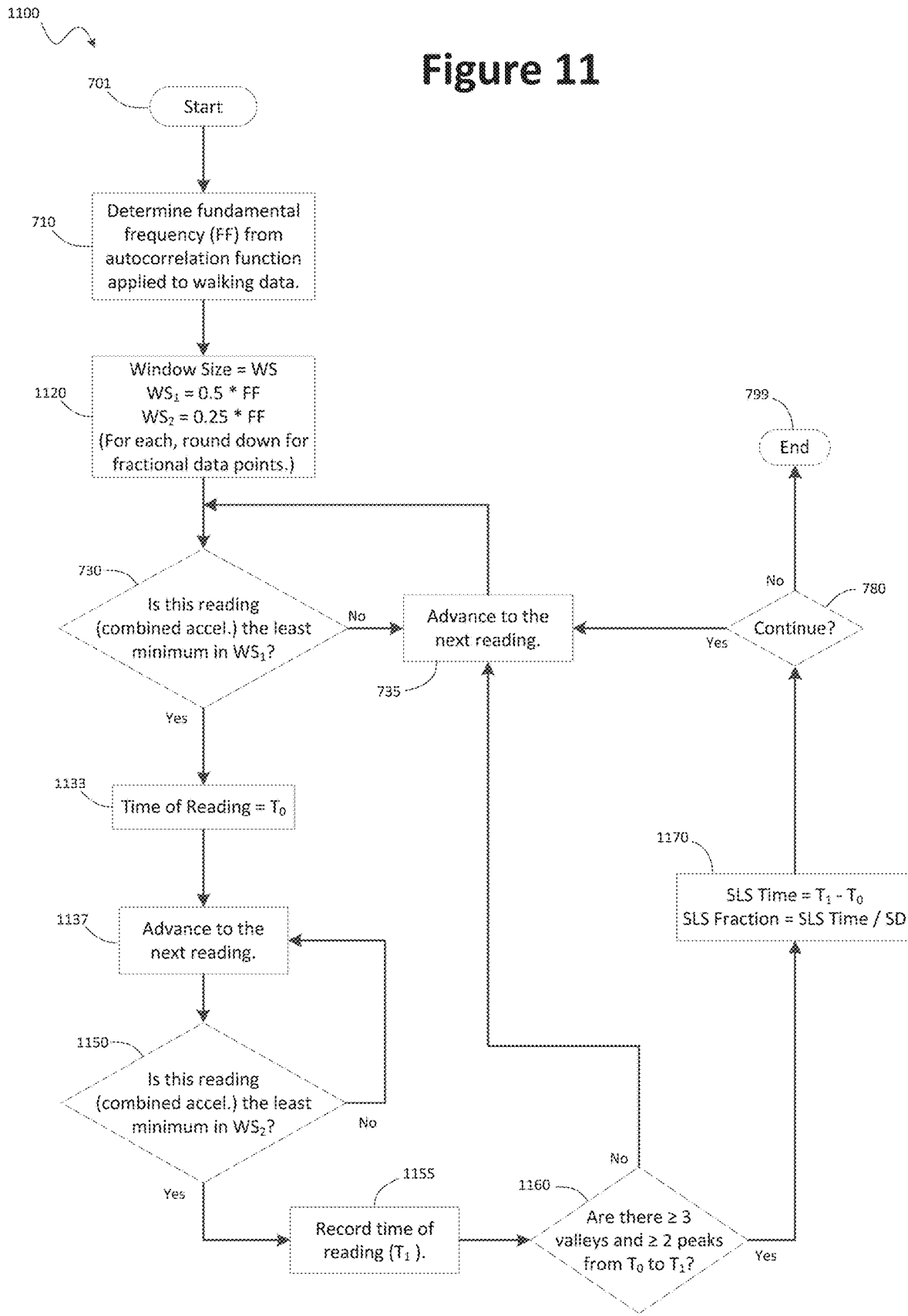
FIG. 11 presents a flow chart illustrating a method for estimating SLS duration, according to certain embodiments of the present disclosure.

FIG. 11 presents a flow chart illustrating an embodiment of a processor-implemented method (1100) for estimating SLS. After the start (701), the fundamental frequency (FF) for a sample of data (combined acceleration of all axes) is determined using an autocorrelation function (710). Windows of two sizes are selected; $WS_1$ is half (0.5) of FF and $WS_2$ is one quarter (0.25) FF (1120). For both windows, window duration is rounded down to the next lowest whole number of accelerometer readings (1120). The method (1100) then queries if the focal reading (the reading being examined) is the lowest local minimum in $WS_1$ (730). If not, analysis proceeds to the next reading (735). If the focal reading is the lowest minimum in $WS_1$, the time at which the focal reading was generated (To) is recorded (1133). Analysis then proceeds to the next reading (1137). The method (1100) then queries if the focal reading is the lowest minimum in WΩ (1150). If not, analysis proceeds to the next reading (1137). If the focal reading is the lowest minimum in $WS_2$, the time at which the focal reading was generated ($T_1$) is recorded (1155). The method (1100) then queries whether there have been at least 3 valleys and two peaks (within the second, shorter window) in the time period from $T_0$ to $T_1$ (1160). If not, analysis proceeds to the next reading (735). If so, the method (1100) estimates the amount of SLS time to be the difference between $T_1$ and $T_0$ (1170). The fraction of the step spent in SLS is estimated as SLS time divided by step duration (SD) (1170). The method (1100) then queries whether to continue (780). If not, the method (1100) ends (799). If analysis continues, analysis proceeds to the next reading (735) where the method (1100) queries if the focal reading is the lowest minimum in $WS_1$ (730). Step 730 effectively scans for the beginning of the next step.

Some embodiments calculate DLS time as the amount of time starting at the second peak as determined by a second (shorter) sliding window to the next valley as determined by the first (longer) sliding window. The "second valley" is the second relative to the beginning of a step defined by a valley determined by the first (longer) sliding window.

Figure 12:
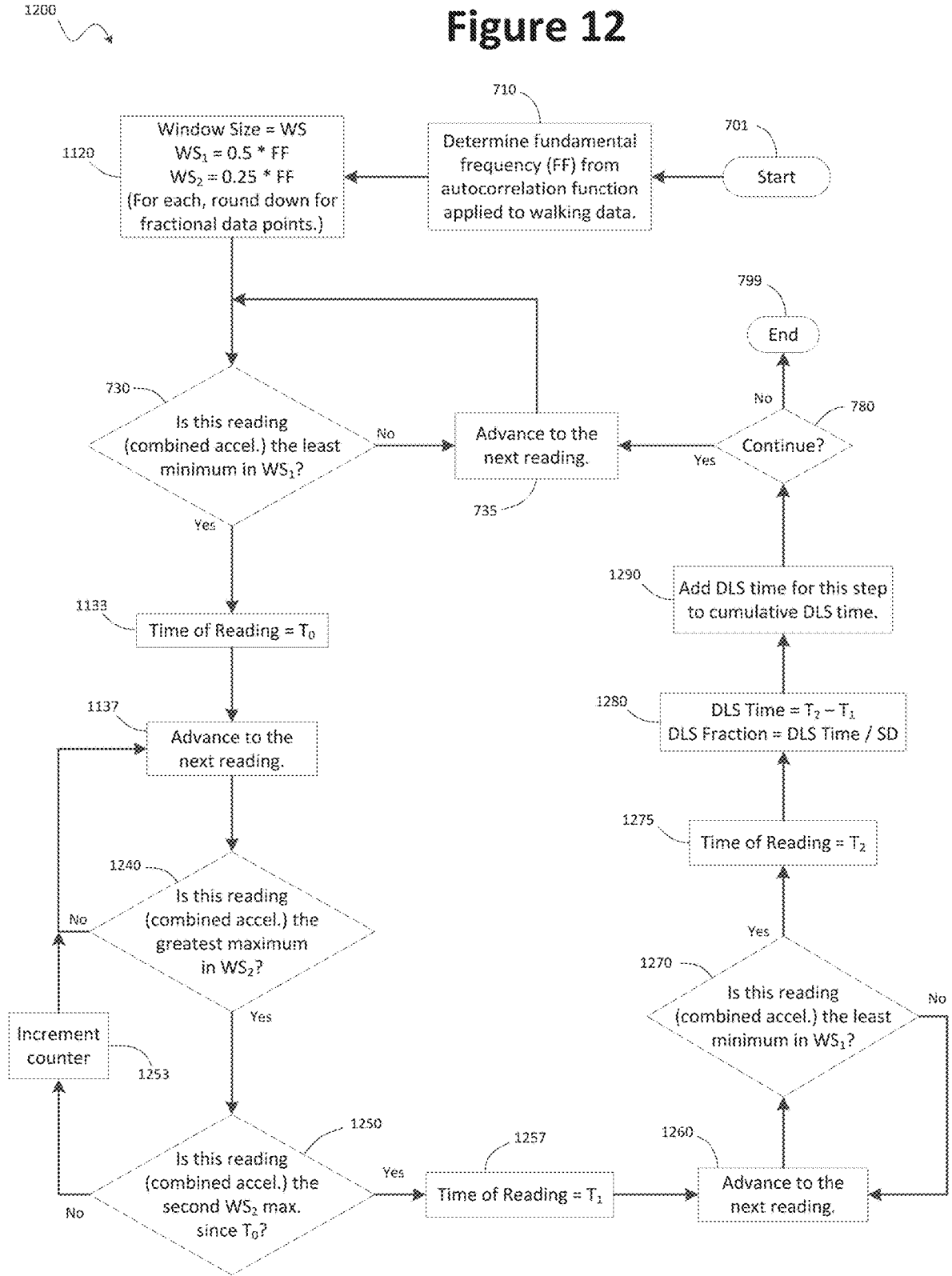
FIG. 12 presents a flow chart illustrating a method for estimating DLS duration, according to certain embodiments of the present disclosure.

FIG. 12 presents a flow chart illustrating an embodiment of a processor-implemented method (1200) for estimating DLS. After the start (701), the fundamental frequency (FF) for a sample of data is determined using an autocorrelation function (710). Windows of two sizes are selected; $WS_1$ is half (0.5) of FF and $WS_2$ is one quarter (0.25) FF (1120). For each window, window duration is rounded down to the next lowest whole number of accelerometer readings (1120). The method (1200) then queries if the focal reading (combined acceleration of all axes) is the lowest minimum in $WS_1$ (730). If not, analysis proceeds to the next reading (735). If the focal reading is the lowest local minimum in $WS_1$, the time at which the focal reading was generated (To) is recorded (1133). Analysis then proceeds to the next reading (1137). The method (1200) then queries whether the focal reading is the greatest maximum in $WS_2$ (1240). If the focal reading is not the greatest local maximum in $WS_2$, analysis advances to the next reading (1137). If the focal reading is the greatest maximum in $WS_2$, the method (1200) queries whether the focal reading is the second maximum (within $WS_2$) to occur since $T_0$ (1250). If not, a counter is incremented (1253) and analysis advances to the next reading (1137). If the focal reading is the second maximum (within $WS_2$) to occur since $T_0$, the time of the focal reading is recorded as $T_1$ (1257). Analysis then proceeds to the next reading (1260). The method (1200) then queries whether the focal reading is the least minimum within $WS_1$ (1270). If not, analysis advances to the next reading (1260). If the focal reading is the least minimum within $WS_1$, the time of the focal reading is stored as $T_2$ (1275). DLS time is estimated as the difference between $T_2$ and $T_1$ (1280). The fraction of the step spent in DLS is estimated as DLS time divided by step duration (1280). The amount of DLS time is then added to a cumulative tally of SLS time during the walk (1290) which, when divided by the duration of the walk, yields the average proportion of DLS time for steps taken during the walk. The method (1200) then queries whether to continue (780). If not, the method (1200) ends (799). If analysis continues, analysis proceeds to the next reading (735) where the method (1200) queries whether the focal reading is the lowest minimum in $WS_1$, effectively scanning for the beginning of the next step (730).

Some embodiments estimate SLS and DLS using threshold crossing points in addition to peaks and valleys. One embodiment, for example, estimates DLS time as the time from a valley marking the beginning of a step to the time at which acceleration readings first exceed a threshold. The valley may be determined, for example, by a sliding window. Correspondingly, some embodiments estimate SLS time as starting when accelerometer readings first exceed a threshold and ending at the valley marking the end of a step.

Figure 13:
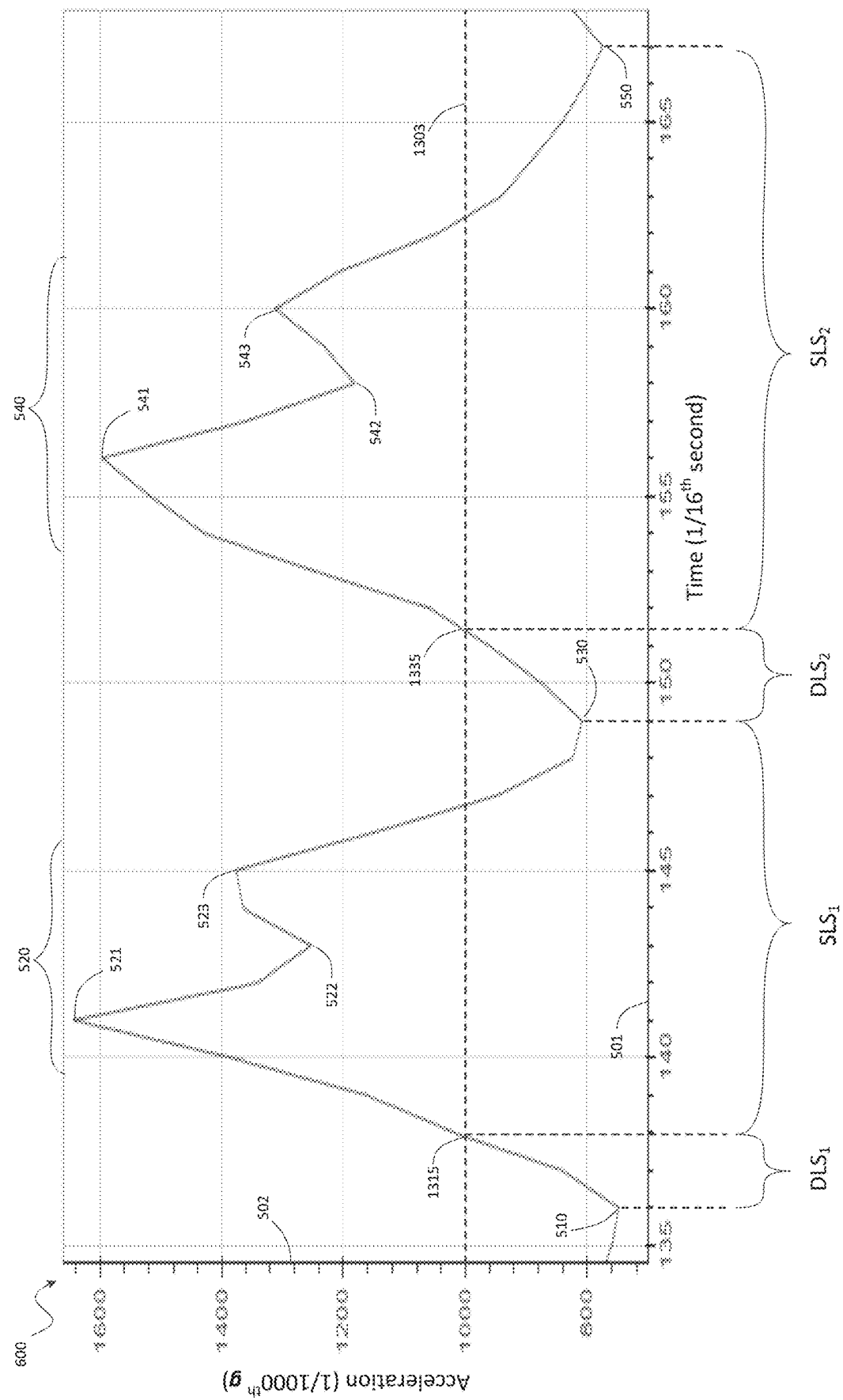
FIG. 13 presents a plot of acceleration of a wrist-worn accelerometer during two steps and illustrates a portion of each step attributed to SLS and to DLS according to certain embodiments of the present disclosure.

FIG. 13 presents the acceleration plot of FIG. 5 and delineates time periods corresponding to the durations of both SLS and DLS, according to certain embodiments. The specified time periods do not necessarily correspond to the times when SLS and/or DLS are occurring but estimate the amount of time spent in SLS and DLS. A horizontal dashed line (1303) at gravitational acceleration (g) represents a threshold set at that level. In this embodiment, the times for SLS and DLS add to the total step duration (SD). For each of the two steps shown in the plot, the DLS time is estimated to be the time from the valley marking the beginning of a step (510, 530) to the first time (within the step) in which acceleration readings exceed threshold 1303 (1315, 1335 respectively). DLS time for the first step (DLS1) is estimated as being the amount of time from valley 510 to threshold crossing 1315, which is approximately 2/16ths (one eighth) of a second. The proportion of the first step spent in DLS is estimated to be DLS1/SD1 or 2/13ths of the step. SLS time for the first step (SLS1) is estimated as being the amount of time from threshold crossing 1315 to valley 530, which is approximately 11/16ths of a second. The proportion of the first step spent in SLS is estimated to be SLS1/SD1 or 11/13ths of the step. DLS time for the second step (DLS2) is estimated as the amount of time from valley 530 to threshold crossing 1335 which is approximately 2.5/16ths of a second. The proportion of the second step spent in DLS is estimated to be DLS2/SD2. or 2.5/18ths of the step. SLS time for the second step (SLS2) is estimated as being the amount of time from threshold crossing 1335 to valley 550, which is approximately 15.5/16ths of a second. The proportion of the first step spent in SLS is estimated to be SLS1/SD1 or 15.5/18ths of the step.

Methods of estimating SLS and DLS, such as that presented visually in FIG. 13, may be executed by processors in a numerical fashion. Crossing of a threshold may, for example, be determined if a reading is greater than a threshold number. Determination of various maxima and minima may be determined using methods including those described herein. For example, a step minimum may be determined if a reading is flanked on either side by higher readings and is the least such inflection point in a window of a given duration.

Figure 14:
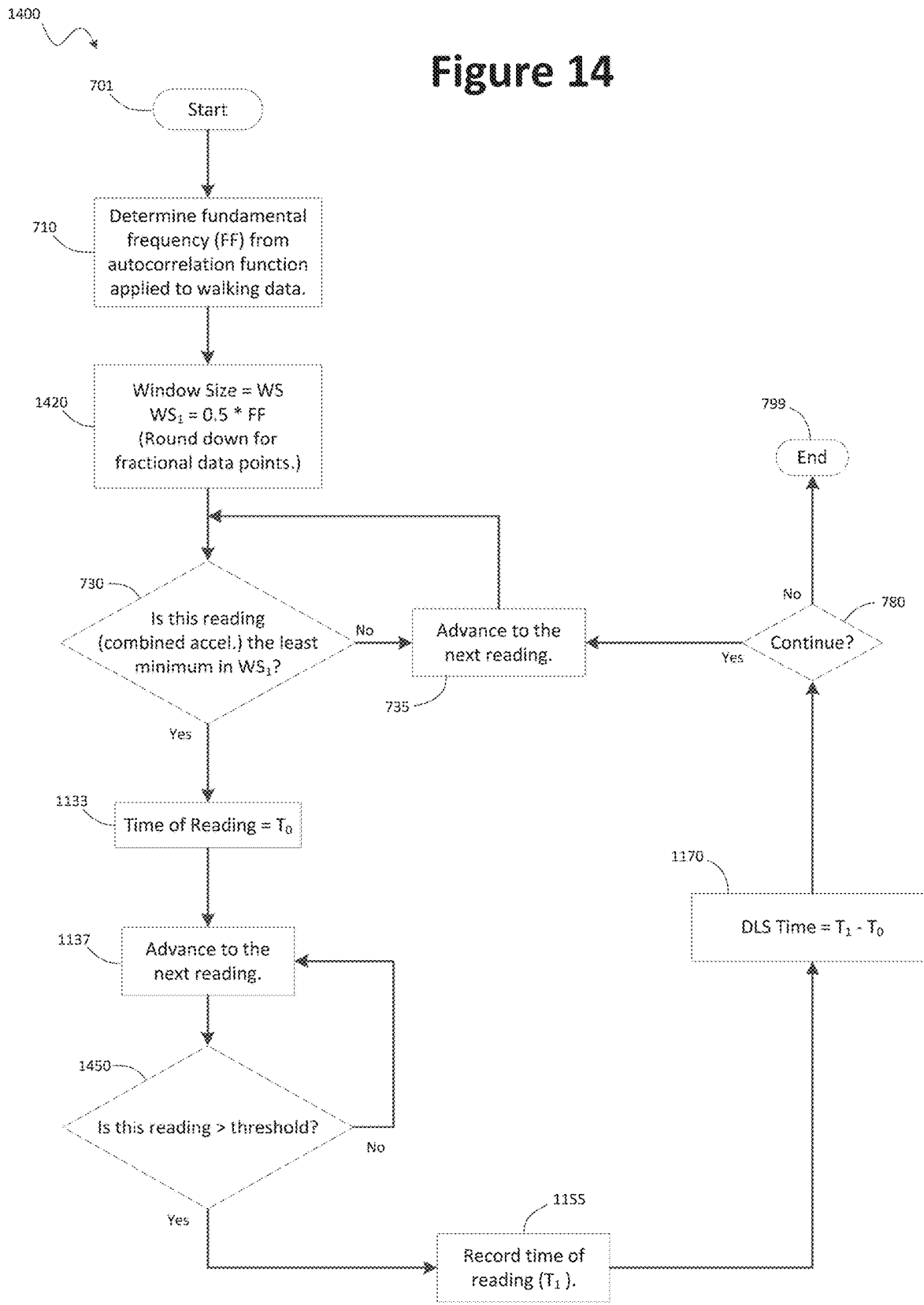
FIG. 14 presents a flow chart illustrating a method for estimating DLS time, according to certain embodiments of the present disclosure.

FIG. 14 presents a flow chart illustrating an embodiment of a processor-implemented method (1400) for estimating DLS. After the start (701), the fundamental frequency (FF) for a sample of data (combined acceleration of all axes) is determined using an autocorrelation function (710). Window size $WS_1$ is half (0.5) of FF (1420). Window duration is rounded down to the next lowest whole number of accelerometer readings (1420). The method (1400) then queries if the focal reading (the reading being examined) is the lowest local minimum in $WS_1$ (730). If not, analysis proceeds to the next reading (735). If the focal reading is the lowest minimum in $WS_1$, the time at which the focal reading was generated (To) is recorded (1133). Analysis then proceeds to the next reading (1137). The method (1400) then queries if the focal reading is the greater than a threshold (1450). In some embodiments, the threshold is 1 g. If not, analysis proceeds to the next reading (1137). If the focal reading is greater than the threshold, the time at which the focal reading was generated ($T_1$) is recorded (1155). The method (1400) estimates the amount of DLS time to be the difference between $T_1$ and $T_0$ (1170). The method (1400) then queries whether to continue (780). If not, the method (1400) ends (799). If analysis continues, analysis proceeds to the next reading (735) where the method (1400) queries if the focal reading is the lowest minimum in $WS_1$ (730). Step 730 effectively scans for the beginning of the next step.

Figure 15:
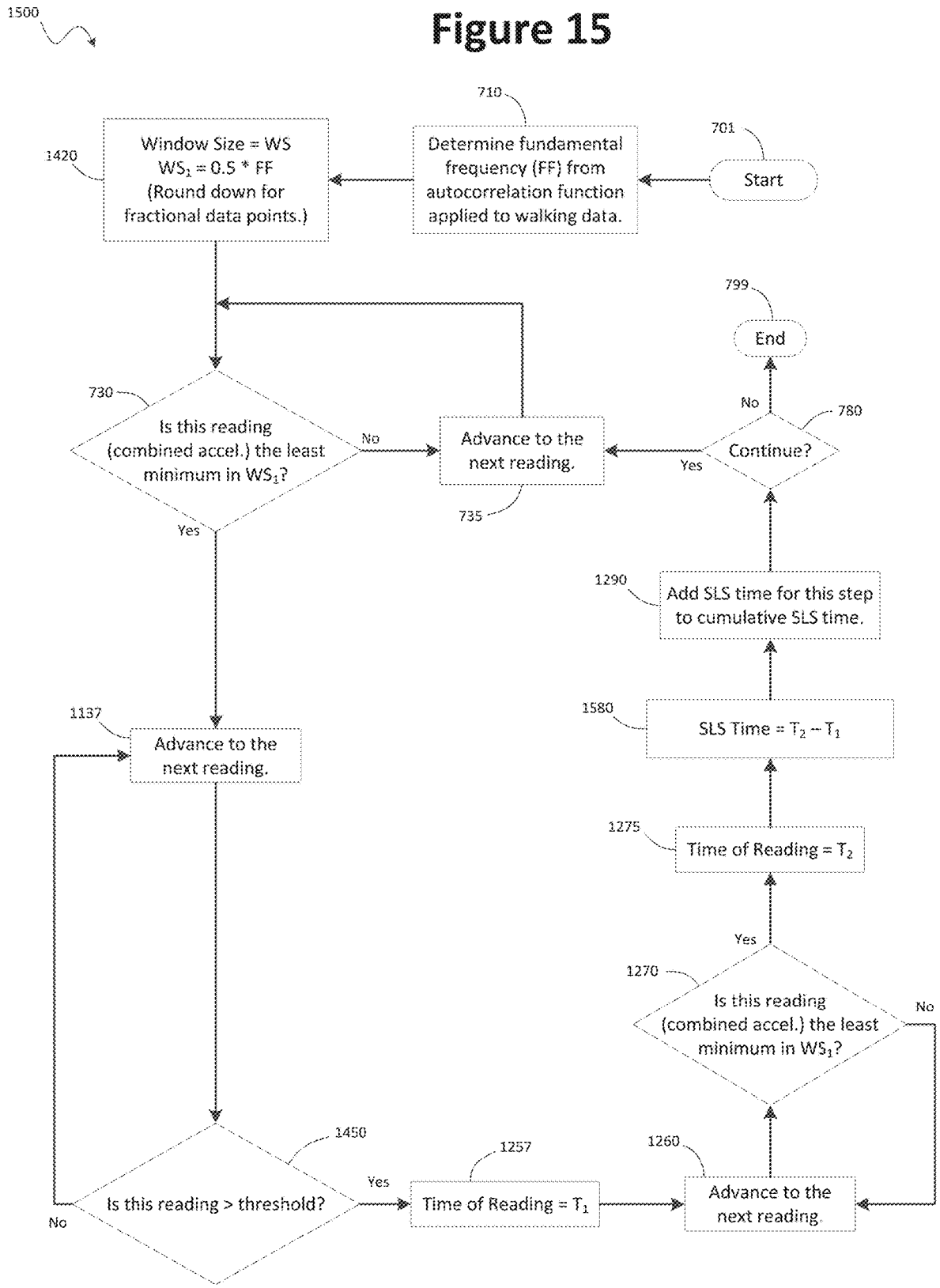
FIG. 15 presents a flow chart illustrating a method for estimating SLS time, according to certain embodiments of the present disclosure.

FIG. 15 presents a flow chart illustrating an embodiment of a processor-implemented method (1500) for estimating SLS. After the start (701), the fundamental frequency (FF) for a sample of data is determined using an autocorrelation function (710). Window size $WS_1$ is half (0.5) of FF (1420). Window duration is rounded down to the next lowest whole number of accelerometer readings (1420). The method (1500) then queries if the focal reading (combined acceleration of all axes) is the lowest minimum in $WS_1$ (730). If not, analysis proceeds to the next reading (735). If the focal reading is the lowest local minimum in $WS_1$, analysis proceeds to the next reading (1137). The method (1500) then queries whether the focal reading is greater than a threshold (1450). In some embodiments, the threshold is 1 g. If the focal reading is not greater than the threshold, analysis advances to the next reading (1137). If the focal reading is greater than the threshold, the time of the focal reading is recorded as $T_1$ (1257). Analysis then proceeds to the next reading (1260). The method (1500) then queries whether the focal reading is the least minimum within $WS_1$ (1270). If not, analysis advances to the next reading (1260). If the focal reading is the least minimum within $WS_1$, the time of the focal reading is stored as $T_2$ (1275). SLS time is estimated as the difference between $T_2$ and $T_1$ (1580). The amount of SLS time is then added to a cumulative tally of SLS time during the walk (1290) which, when divided by the duration of the walk, yields the average proportion of SLS time for steps taken during the walk. The method (1500) then queries whether to continue (780). If not, the method (1500) ends (799). If analysis continues, analysis proceeds to the next reading (735) where the method (1500) queries if the focal reading is the lowest minimum in $WS_1$ (730), effectively scanning for the beginning of the next step.

Step Width

Step width is the component of the distance between the contact points of the feet that is perpendicular to the direction the individual is moving. Step width may be an important indicator of conditions such as obesity and balance disorders. Some embodiments estimate step width as a function of acceleration along an axis approximately parallel to the user's lateral anatomical axis. Of these embodiments, some estimate step width as a function of the double integral. For example, some of these embodiments multiply the double integral by a coefficient selected to accommodate the particularities of a specific accelerometer or type of accelerometer. An integral, or area under the signal curve, may be estimated using a Riemann sum or other techniques known to those in the art. The integral may taken from the beginning of the step to the end of the step as determined by various methods discussed herein.

Some embodiments screen data on a Z axis to determine whether the data should be discarded from consideration. For example, some embodiments do not estimate width of a particular step if readings on a Z axis of the accelerometer exceed a threshold. Readings from the Z axis exceeding a threshold may indicate that part of acceleration in the direction of the Z axis is caused by rotation of the wrist, waist, or other body part to which the accelerometer is coupled rather than linear lateral motion.

Once estimated, step width may be used with other estimated measures. For example, some embodiments calculate a step ratio—the ratio of step length to step width. Step ratio may be more informative than step width alone since step width tends to increase with step length even among healthy individuals.

Figure 16:
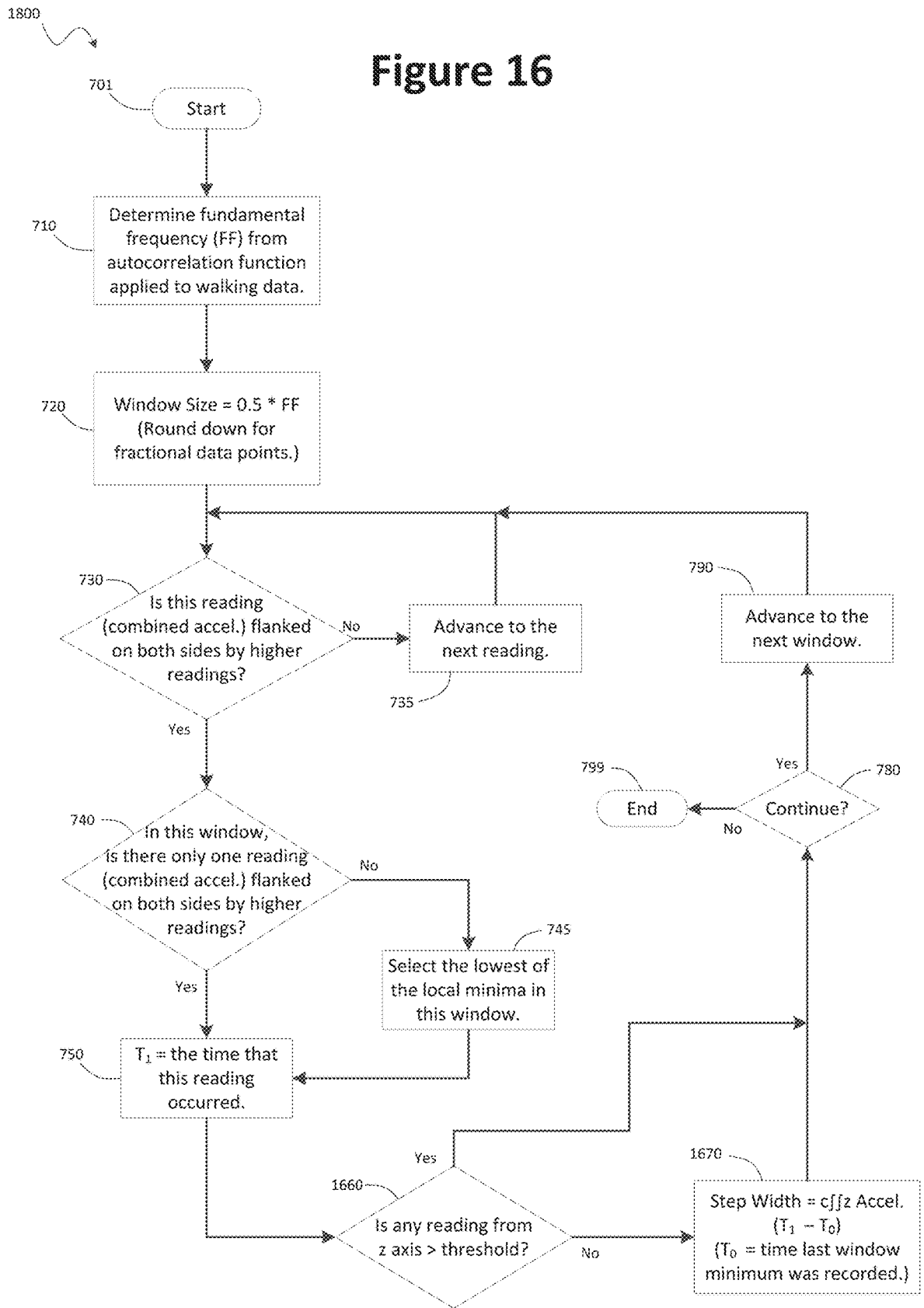
FIG. 16 presents a flow chart illustrating a method for estimating step width, according to certain embodiments of the present disclosure.

FIG. 16 presents a flow chart illustrating an embodiment of a processor-implemented method (1600) for estimating step width, according to the present disclosure. After the start (701), the fundamental frequency is determined using an autocorrelation function (710). Window size is set at half the fundamental frequency of the autocorrelation (720). If half the time of the fundamental frequency includes a fraction of an accelerometer reading, the window size rounds down to the next whole number of readings (720). Starting with the first reading in a window, the method (1600) queries whether the reading is lower than both the immediately previous reading and the immediately following reading (730). If not, analysis proceeds to the next reading (735). If the reading is a local minimum (flanked by greater readings), the method then queries whether the reading is the only local minimum in its window (740). If so, the single local minimum is selected. If there are one or more other local minima in the window, the lowest of the local minima is selected (745). The time of the selected local minimum ($T_1$) is then accessed (750). The method (1600) then queries whether any reading from the z axis of the accelerometer exceeds a threshold (1660). If so and if analysis continues (780), analysis proceeds to the next window (790). If not, step width is estimated as a constant (c) multiplied by the double integral of acceleration on the z axis from time $T_0$ to time $T_1$ (1670). To is the time at which the immediately previous window minimum (lowest minimum in the window) occurred. The method (1600) then queries whether to continue (780). If so, analysis proceeds to the next window (790). If not, the method (1600) ends (799).

Gait Symmetry

In a healthy gait, the steps of one foot tend to be similar to those of the other. Differences between the left foot and right foot with respect to parameters such as those discussed herein may indicate a problem manifesting itself in an individual's gait. Some device embodiments may compare gait metrics of the left leg to those of the right leg to assess gait symmetry. Embodiments may use averages or other measures of central tendency for gait parameters of each foot. Embodiments may compare gait metrics of the left leg to those of the right leg over a variety of time periods depending on the particular application of the gait symmetry measurement. For example, some embodiments may assess gait symmetry based on averages of the last minute. Some embodiments may assess gait symmetry from the beginning of an episode of walking. Embodiments need not ascertain which metrics are attributable to the left leg and which are attributable to the right leg. An embodiment may assess gait symmetry if it can distinguish the activity attributable to one leg from activity attributable to the other, even without determining which leg is the left or right.

Some embodiments may assess gait in real time and provide the user feedback regarding his or her gait symmetry. Some embodiments may provide automated gait coaching. For example, a system embodiment may advise the user to take longer steps with the left leg.

Gait Variability

Variation among steps of a single leg and/or variation among strides may also be indicators of gait health, with higher variation indicating potential problems manifesting in gait. However, high variation of a gait parameter does not necessarily indicate a problem. For example, walking on uneven terrain may cause an individual with an otherwise healthy gait to have high variability among steps or strides. Gait variation may refer to the variation of any gait parameter and variation may be quantified using a variety of measures such as variance, standard deviation, and average deviation.

Some embodiments may assess gait in real time and provide the user feedback regarding his or her gait symmetry. Some embodiments may provide automated gait coaching. For example, a system embodiment may provide an audible and/or visible cadence beat and advise the user to take steps on the beat, thus encouraging more regular step duration.

The above description is neither exclusive nor exhaustive and is intended neither to describe all possible embodiments (also called "examples") nor to limit the scope of the claims. Claimed embodiments may include elements in addition to those in the described embodiments and, in some cases, may contain only a subset of the elements described in a particular embodiment. Embodiments may contain any combination of elements in the described embodiments in addition to elements not expressly described. As used herein, the articles "a" and "an" may include one or more than one of the noun modified by either without respect to other uses of phrases such as "one or more" or "at least one." The word "or" is used inclusively unless specified otherwise. Terms such as "first," "second," "third" and so forth are used as labels to distinguish elements and do not indicate sequential order unless otherwise indicated. In addition to the embodiments described above, embodiments include any that would fall within the scope of the Claims, below.

What is claimed is:

1. A system for monitoring gait of a user comprising:
   a wrist-worn accelerometer configured to measure a plurality of acceleration readings for an arm of a user over a time period;
   one or more processors communicatively coupled to one or more non-transitory computer-readable storage media, the one or more processors configured to:
      receive the plurality of acceleration readings for the arm of the user;
      determine, based on one or more of the plurality of acceleration readings for a first window within the time period, a first angular measure corresponding to a first arm angle at a first position of an arm swing;
      determine, based on one or more of the plurality of acceleration readings for a second window within the time period and subsequent to the first window, a second angular measure corresponding to a second arm angle at a second position of the arm swing;
      determine an arc length for a hand of the user during the arm swing based at least in part on the first angular measure, the second angular measure, and an arm length of the user; and
      determine a step length of the user based at least in part on the arc length for the hand of the user; and
   a display communicatively coupled to the one or more processors and configured to provide a real time suggestion based at least in part on the step length, wherein the real time suggestion comprises a suggestion to take longer steps.

2. The system of claim 1, wherein the one or more processors are further configured to:
   identify a first minimum reading from the one or more of the plurality of acceleration readings for during the first window; and
   identify a second minimum reading from the one or more of the plurality of acceleration readings for the second window, wherein:
      (i) the second window is equal in duration to the first window,
      (ii) a time of the first minimum reading coincides with the second position, and
      (iii) a time of the second minimum reading coincides with the second position.

3. The system of claim 2, wherein (i) the one or more processors are further configured to determine a fundamental frequency using an autocorrelation function applied to the plurality of acceleration readings and (ii) a duration of the first window is a fraction of the fundamental frequency.

4. The system of claim 1, wherein the one or more processors are further configured to (i) compare a first step length of a left leg to a second step length of a right leg to determine a measure of symmetry and (ii) provide user feedback associated with the measure of symmetry.

5. The system of claim 1, wherein the one or more processors are further configured to: determine a variability measure of a plurality of step lengths; and provide user feedback associated with the variability measure.

6. A method comprising:
   receiving, by one or more processors and from a wrist-worn accelerometer configured to measure a plurality of acceleration readings for an arm of a user over a time period, the plurality of acceleration readings for the arm of the user over the time period;
   determining, by the one or more processors based on one or more of the plurality of acceleration readings for a first window within the time period, a first angular measure corresponding to a first arm angle at a first position of an arm swing;
   determining, by the one or more processors based on one or more of the plurality of acceleration readings for a second window within the time period and subsequent to the first window, a second angular measure corresponding to a second arm angle at a second position of the arm swing;
   determining, by the one or more processors, an arc length for a hand of the user during the arm swing based at least in part on the first angular measure, the second angular measure, and an arm length of the user;
   determining, by the one or more processors, a step length of the user based at least in part on the arc length for the hand of the user; and
   providing, by the one or more processors and via a display, a real time suggestion based at least in part on the step length, wherein the real time suggestion comprises a suggestion to take longer steps.

7. The method of claim 6 further comprising:
   identifying a first minimum reading from the one or more of the plurality of acceleration readings for the first window; and
   identifying a second minimum reading from the one or more of the plurality of acceleration readings for the second window, wherein:

(i) the second window is equal in duration to the first window, (ii) a time of the first minimum reading coincides with the first position, and (iii) a time of the second minimum reading coincides with the second position.

8. The method of claim 7, further comprising:

determining a fundamental frequency using an autocorrelation function applied to the plurality of acceleration readings, wherein a duration of the first window is a fraction of the fundamental frequency.

9. The method of claim 6 further comprising comparing step lengths of a left leg to step lengths of a right leg to determine a measure of symmetry and provide user feedback associated with the measure of symmetry.

10. The method of claim 6 further comprising:

determining a variability measure of a plurality of step lengths; and providing user feedback associated with the variability measure to the display.

11. One or more non-transitory computer-readable storage media including instructions that, when executed by one or more processors, cause the one or more processors to:

receive, from a wrist-worn accelerometer configured to measure a plurality of acceleration readings for an arm of a user over a time period, the plurality of acceleration readings for the arm of the user over the time period;

determine, based on one or more of the plurality of acceleration readings for a first window within a time period, a first angular measure corresponding to a first arm angle at a first position of an arm swing;

determine, based on one or more of the plurality of acceleration readings for a second window within the time period and subsequent to the first window, a second angular measure corresponding to a second arm angle at a second position of the arm swing;

determine an arc length for a hand of the user during the arm swing based at least in part on the first angular measure, the second angular measure, and an arm length of the user;

determine a step length of the user based at least in part on the arc length for the hand of the user; and provide, via a display, a real time suggestion based at least in part on the step length, wherein the real time suggestion comprises a suggestion to take longer steps.

12. The one or more non-transitory computer-readable storage media of claim 11, wherein the one or more processors are further caused to:

identify a first a minimum reading from the one or more of the plurality of acceleration readings for the first window; and identify a second minimum reading from the one or more of the plurality of acceleration readings for the second window, wherein:

(i) the second window is equal in duration to the first window, (ii) a time of the first minimum reading coincides with the first position, and (iii) a time of the second minimum reading coincides with the second position.

13. The one or more non-transitory computer-readable storage media of claim 12, wherein (i) the one or more processors are further caused to determine a fundamental frequency using an autocorrelation function applied to the plurality of acceleration readings, and (ii) a duration of the first window is a fraction of the fundamental frequency.

14. The one or more non-transitory computer-readable storage media of claim 11, wherein the one or more processors are further caused to (i) compare a first step length of a left leg to a second step length of a right leg to determine a measure of symmetry and (ii) provide user feedback associated with the measure of symmetry.

15. The one or more non-transitory computer-readable storage media of claim 11, wherein the one or more processors are further caused to:

determine a variability measure of a plurality of step lengths; and provide user feedback associated with the variability measure.

* * * * *

UNITED STATES PATENT AND TRADEMARK OFFICE
CERTIFICATE OF CORRECTION

PATENT NO. : 12,350,035 B2
APPLICATION NO. : 16/921270
DATED : July 8, 2025
INVENTOR(S) : Gregory R. Romrell et al.

It is certified that error appears in the above-identified patent and that said Letters Patent is hereby corrected as shown below:

In the Claims

In Column 18, Line 7, Claim 2, delete "for during" and insert -- for --, therefor.

In Column 18, Line 16, Claim 2, delete "second" and insert -- first --, therefor.

In Column 19, Line 20, Claim 10, delete "measure to the display." and insert -- measure. --, therefor.

In Column 20, Line 9, Claim 12, delete "first a" and insert -- first --, therefor.

Signed and Sealed this
Eleventh Day of November, 2025

John A. Squires
*Director of the United States Patent and Trademark Office*